(12) United States Patent
Tsuji et al.

(10) Patent No.: US 12,089,852 B2
(45) Date of Patent: *Sep. 17, 2024

(54) ENDOSCOPE CLIP AND OPERATION METHOD FOR CLIP ARM

(71) Applicant: OLYMPUS CORPORATION, Hachioji (JP)

(72) Inventors: Tomohiro Tsuji, Tachikawa (JP); Kensuke Uesaka, Hino (JP); Yuya Hidaka, Fuchu (JP); Naoki Fujikawa, Hachioji (JP); Akane Yasukawa, Hachioji (JP); Naoki Takizawa, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 717 days.

This patent is subject to a terminal disclaimer.

(21) Appl. No.: 17/313,252

(22) Filed: May 6, 2021

(65) Prior Publication Data
US 2021/0267602 A1   Sep. 2, 2021

Related U.S. Application Data

(63) Continuation of application No. PCT/JP2018/041599, filed on Nov. 9, 2018.

(51) Int. Cl.
*A61B 17/122* (2006.01)
*A61B 17/00* (2006.01)

(52) U.S. Cl.
CPC ...... *A61B 17/122* (2013.01); *A61B 17/00234* (2013.01); *A61B 2017/00296* (2013.01)

(58) Field of Classification Search
CPC ............ A61B 17/122; A61B 17/00234; A61B 2017/00296; A61B 2017/00367;
(Continued)

(56) References Cited

U.S. PATENT DOCUMENTS

| 6,210,398 B1* | 4/2001 | Ouchi | A61B 17/2909 |
| | | | 600/184 |
| 2002/0045909 A1* | 4/2002 | Kimura | A61B 17/083 |
| | | | 606/151 |
| 2002/0128667 A1* | 9/2002 | Kobayashi | A61B 17/1227 |
| | | | 606/139 |
| 2003/0083677 A1* | 5/2003 | Damarati | A61B 17/122 |
| | | | 606/151 |

(Continued)

FOREIGN PATENT DOCUMENTS

| CN | 107405046 A | 11/2017 |
| JP | S50-038691 U | 4/1975 |

(Continued)

OTHER PUBLICATIONS

English Translation of the description to the JP 2013085859 (Year: 2013).*

(Continued)

*Primary Examiner* — Mohamed G Gabr
*Assistant Examiner* — Aman Kumar Mann
(74) *Attorney, Agent, or Firm* — Oliff PLC

(57) ABSTRACT

Provided is an endoscope clip and an operation method for a clip. The clip includes a clip arm that is configured to be transitioned between a first, second and third configurations. The clip includes a slider to operate the clip arm to be transitioned between the configurations, and a limiter configured to restrict movement of the slider so as to restrict the transition of the clip arm from one configuration to another of the configurations.

18 Claims, 20 Drawing Sheets

(58) Field of Classification Search
CPC .... A61B 2017/00407; A61B 2090/034; A61B 2090/3954; A61B 17/1285; A61B 17/1227
See application file for complete search history.

(56) References Cited

U.S. PATENT DOCUMENTS

| | | | | |
|---|---|---|---|---|
| 2006/0190015 | A1* | 8/2006 | Matsuno | A61B 17/122 606/142 |
| 2015/0018848 | A1 | 1/2015 | Kappel et al. | |
| 2015/0112367 | A1 | 4/2015 | Damarati | |
| 2017/0215886 | A1* | 8/2017 | Muyari | A61B 17/122 |
| 2020/0113572 | A1* | 4/2020 | Tsuchiya | A61B 17/1285 |

FOREIGN PATENT DOCUMENTS

| | | | |
|---|---|---|---|
| JP | 2010-136818 A | | 6/2010 |
| JP | 2013-085860 A | | 5/2013 |
| JP | 2013085859 A | * | 5/2013 |
| JP | 5750620 B2 | | 7/2015 |
| WO | 2018/011846 A1 | | 1/2018 |
| WO | 2018/011847 A1 | | 1/2018 |

OTHER PUBLICATIONS

Feb. 5, 2019 International Search Report issued in International Patent Application No. PCT/JP2018/041599.
Sep. 21, 2023 Office Action issued in Chinese Patent Application No. 201880099212.6.
Oct. 17, 2022 Extended European Search Report issued in European Patent Application No. 18939358.0.
Sep. 12, 2023 Office Action issued in Chinese Patent Application No. 201880099211.1.
Feb. 5, 2019 International Search Report issued in International Patent Application No. PCT/JP2018/041600.

* cited by examiner

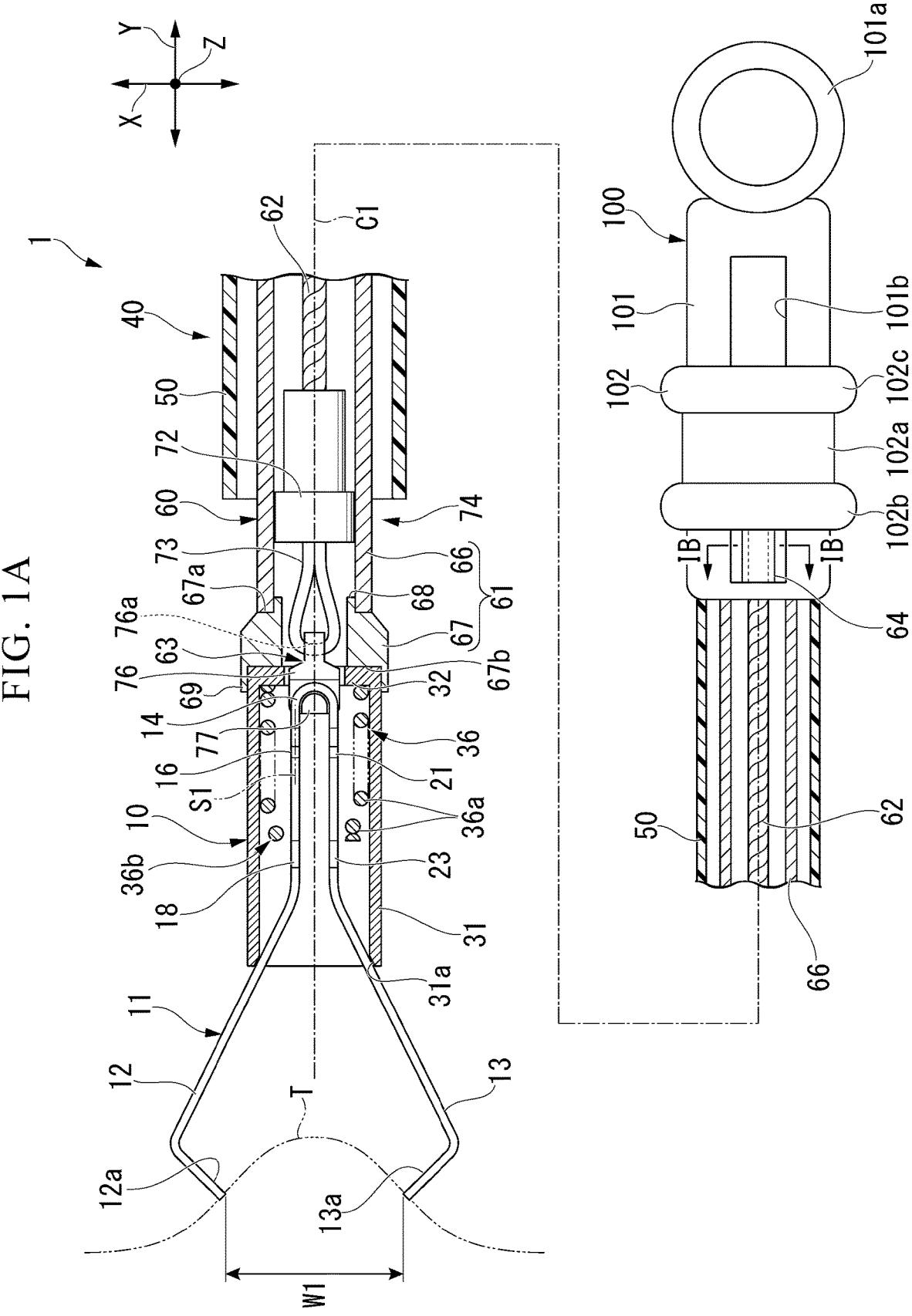

ENDOSCOPE CLIP AND OPERATION METHOD FOR CLIP ARM

TECHNICAL FIELD

The present disclosure relates to an endoscope clip configured for ligating tissues and an operation method for clip arm.

This application is a continuation application of PCT International Application No. PCT/JP2018/041599, filed on Nov. 9, 2018. The content of the PCT International Application is incorporated herein by reference.

BACKGROUND ART

Conventionally known is an endoscope clip which is introduced into the body of a patient via a channel of an endoscope for a usage of ligating the openings and blood vessels formed in the tissue. An endoscopic treatment tool as described in Japanese Patent (Granted) No. 5750620 is known as such endoscope clip.

The endoscope treatment tool described in Japanese Patent (Granted) No. 5750620 includes a clip unit and a treatment tool body.

The clip unit has a clip main body, a pressing tube, and a spiral spring. The clip main body has a first arm and a second arm. The first arm and the second arm are separated from each other with a space between a distal end of the first arm and a distal end of the second arm in a natural state.

The treatment tool main body has an outer tube, an insertion portion, and an operating member. The insertion portion is inserted through the outer tube so as to be advanceable and retractable, and the insertion portion has a sheath, an operation wire, and a connection member. The operation wire is inserted into the sheath, wherein a distal end thereof is connected to the connection member, and a proximal end thereof is connected to a slider described below. The connection member is provided to connect the clip main body and the operation wire. The operating member is attached to a proximal end side of the insertion portion, and the operating member has an operating portion main body, a slider, and a breaking mechanism. The slider is configured to be advanceable and retractable with respect to the operating portion main body by engaging with a slit of the operating portion main body. The breaking mechanism is built in the operating member. When a tension applying to the breaking mechanism reaches or exceeds a predetermined tensile strength, the breaking mechanism is broken.

The endoscope treatment tool disclosed in Japanese Patent (Granted) No. 5750620 is used as follows.

An operator inserts the endoscope having the channel into the body of the patient. Next, the operator inserts the outer tube from the proximal end portion of the channel of the endoscope and projects the outer tube from the distal end portion of the channel of the endoscope. Subsequently, the operator pulls the outer tube back with respect to the insertion portion of the treatment tool main body to cause the clip main body to project from the distal end side of the outer tube. As a result, the first arm and the second arm of the clip main body enter an open configuration in which there is a gap generated between the first arm and the second arm.

When the operator directs the clip unit toward the target tissue inside the body of the patient while observing the inside of the body of the patient using the endoscope, the target tissue is located between the first arm and the second arm. In this state, when the operator pulls the operation wire toward the proximal end side, the first arm and the second arm are brought into a closed configuration in which the first arm and the second arm are closed so as to grasp the target tissue. When the operator further pulls the operation wire toward the proximal side, the target tissue is moved toward the proximal side while being grasped by the clip main body. Even when the target tissue is grasped by the clip main body, when the operator pushes the operation wire toward the distal end side, the first arm and the second arm of the clip main body enter the open configuration such that it is possible to grasp the target tissues again.

SUMMARY

According to an aspect of the present disclosure, an endoscope clip has a clip arm having a first arm and a second arm, the clip arm configured to be transitioned between a closed configuration in which the first arm and the second arm are closed, a first open configuration in which the first arm and the second arm are separated from each other by a first distance larger than a distance between the first arm and the second arm in the closed configuration, and a second open configuration in which the first arm and the second arm are separated from each other by a second distance larger than the first distance; a handle; a slider configured to operate the clip arm to be transitioned between the closed configuration, the first open configuration, and the second open configuration by moving relative to the handle; and a limiter configured to restrict the relative movement of the slider with respect to the handle so as to restrict transition of the clip arm from the first open configuration to the second open configuration.

According to another aspect of the present disclosure, an endoscope clip includes a clip arm; a sheath through which the clip arm is insertable; an operation portion configured to operate the clip arm to an accommodation configuration in which the clip arm is accommodated in the sheath, a first protrusion configuration in which the clip arm protrudes from the sheath at a first clip length from the sheath, and a second protrusion configuration in which the clip arm protrudes from the sheath at a second clip length from the sheath that is larger than the first clip length; and a restrictor configured to perform a restriction to selectively restrict the clip arm from being transitioned from the first protrusion configuration to the second protrusion configuration.

According to a further aspect of the present disclosure, an operation method for a clip, the clip including a clip arm with a first arm and a second arm, the clip arm configured to be transitioned between a closed configuration in which the first arm and the second arm are closed, a first open configuration in which the first arm and the second arm are separated from each other by a first distance larger than a distance between the first arm and the second arm in the closed configuration, and a second open configuration in which the first arm and the second arm are separated from each other by a second distance larger than the first distance, and a limiter configured to restrict transition of the clip arm from the first open configuration to the second open configuration, the operation method has a step of releasing restriction by the limiter; and after releasing the restriction of the limiter, and when the restriction by the limiter is released, causing the clip arm to move from the first open configuration to the second open configuration.

BRIEF DESCRIPTION OF DRAWINGS

FIG. 1A is a cross-sectional view schematically showing a broken part of a lateral surface of an endoscope clip according to a first embodiment of the present disclosure.

DESCRIPTION OF EMBODIMENTS

First Embodiment

Hereinafter, a configuration of an endoscope clip according to a first embodiment of the present invention will be described with reference to FIGS. 1A to 19.

The endoscope clip 1 according to the present embodiment is used by being inserted into a body of a patient body through a channel formed in an endoscope (not shown). In the present specification, a side on which the endoscope operation portion for the operator to operate the endoscope is located is defined as a proximal side, and a side on which a distal end portion of the endoscope inserted into the body is located is defined as a distal end side.

Figure 1B:
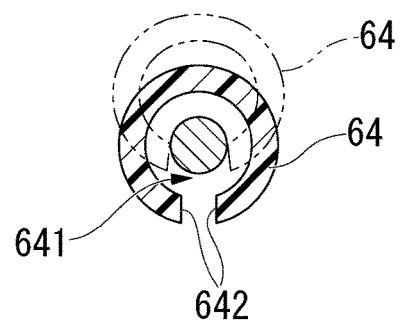
FIG. 1B is a cross-sectional view showing a limiter in the endoscope clip according to the present embodiment that is broken along a cutting line IB-IB shown in FIG. 1A and viewed from a proximal end side.
Figure 2:
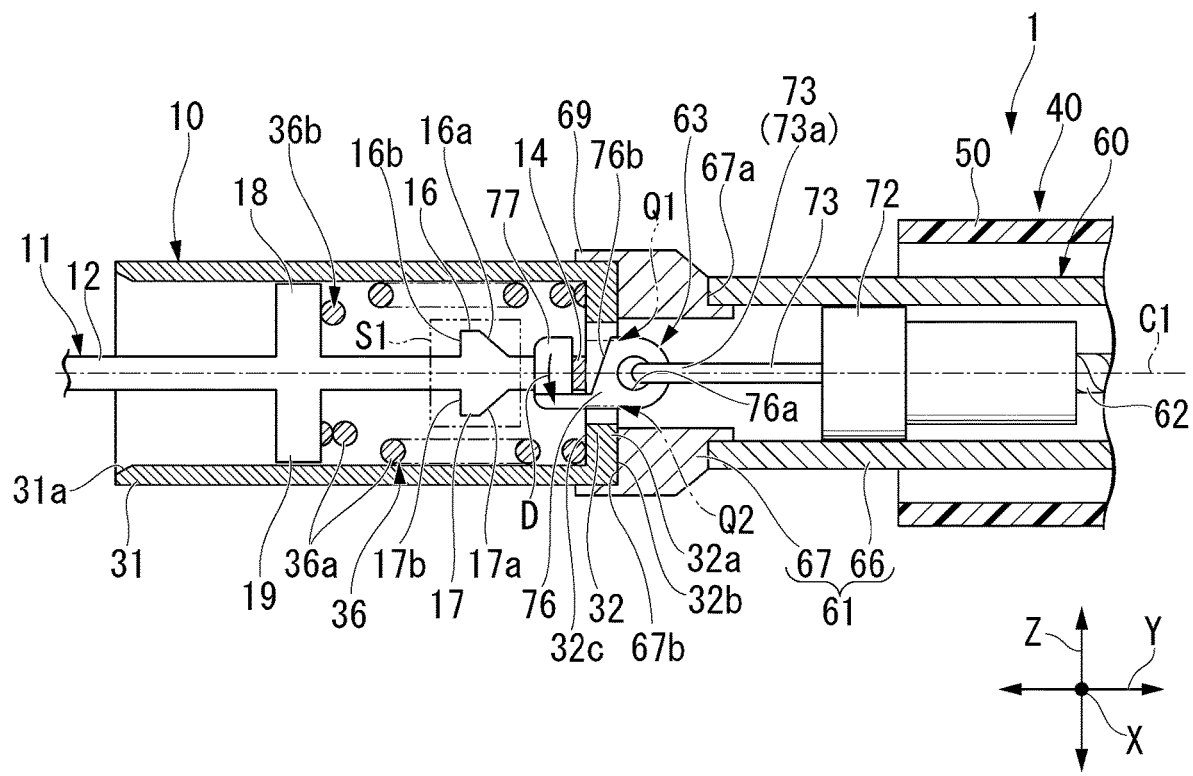
FIG. 2 is a cross-sectional planar view schematically showing part of the distal end portion of the endoscope clip according to the present embodiment.

As shown in FIG. 1A and FIG. 2, the endoscope clip 1 includes a clip unit (hereinafter, described as "clip") 10 and a treatment tool main body 40. The clip 10 is detachably connected to a distal end portion of the treatment tool main body 40.

Figure 3:
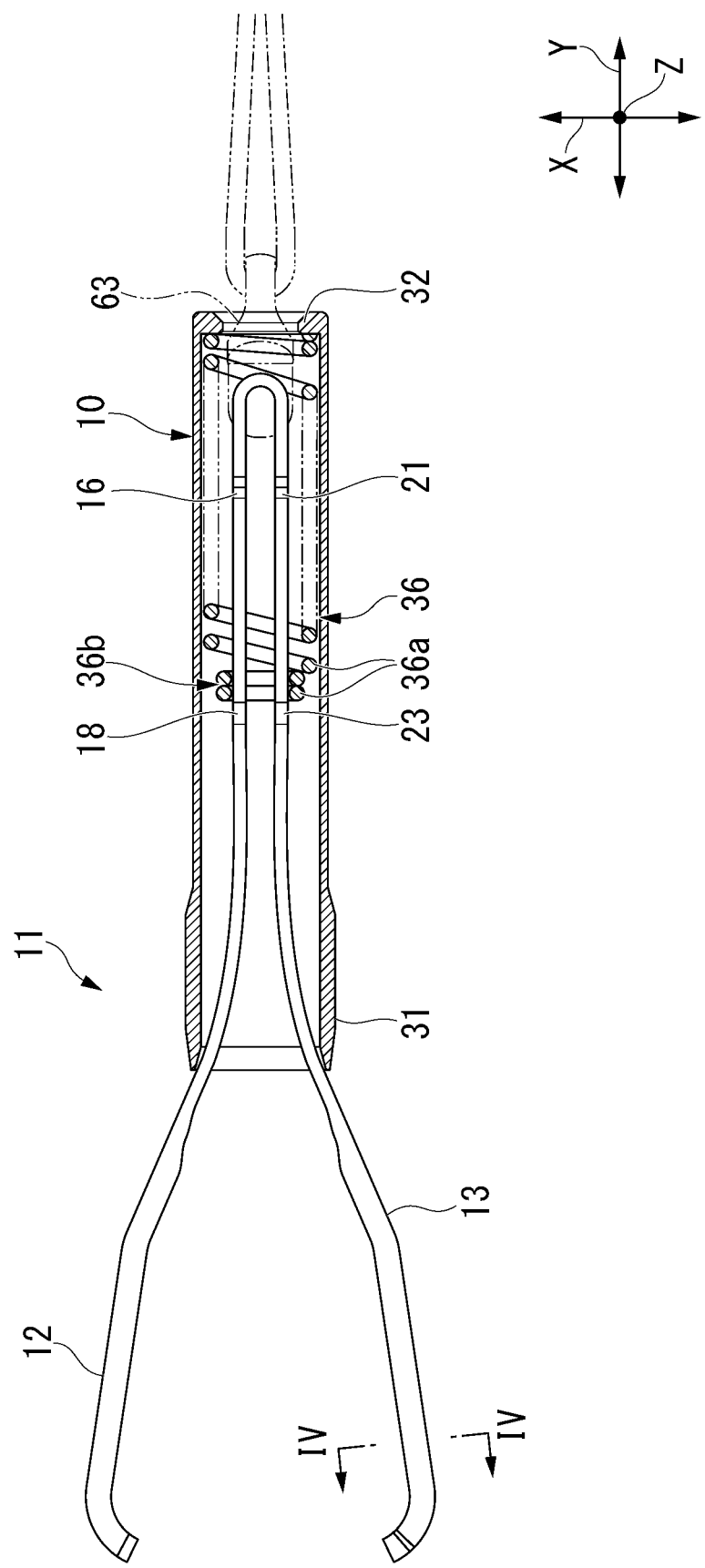
FIG. 3 is a cross-sectional side view showing the endoscope clip according to the present embodiment.

FIG. 1A and FIG. 2 are cross-sectional views of the clip 10 by the plane through an axis C1 of a pressing tube 31 described below. FIG. 3 is a cross-sectional side view of the clip 10.

(Configuration of Clip 10)

As shown in FIG. 1A and FIG. 2, the clip 10 includes an arm portion 11, a pressing tube 31, and a coil spring (elastic member) 36.

The pressing tube 31 is formed in a cylindrical shape and has an inner diameter into which a proximal end portion of the arm portion 11 is able to enter. That is, a lumen into which the arm portion 11 having the first arm 12 and the second arm 13 may enter is formed in the pressing tube 31. The coil spring 36 is configured on an inner wall of the pressing tube 31.

These members including the arm portion 11 that configure the clip 10 are made of a material such as a cobalt chrome alloy, titanium, or stainless steel. The clip 10 may also be configured to be observable under MRI (Nuclear Magnetic Resonance Imaging) fluoroscopy.

The arm portion 11 has a first arm 12, a second arm 13, and a central portion 14. The first arm 12 and the second arm 13 are configured to extend from the proximal end side toward the distal end side and are arranged to face each other. The central portion 14 is located between the proximal end portion of the first arm 12 and the proximal end portion of the second arm 13.

In a natural state, the first arm 12 and the second arm 13 are separated from each other, and a distance between the first arm 12 and the second arm 13 increases along a direction from the proximal end side toward the distal end side. The recitation "natural state" refers to a state in which an external force is not applied to the arm portion 11. For example, a state in which a force by an inner circumferential surface of the pressing tube 31 does not apply to the first arm 12 and the second arm 13 of the arm portion 11 is the natural state. A claw 12a extending toward the second arm 13 side is formed at the distal end portion of the first arm 12.

Figure 4:
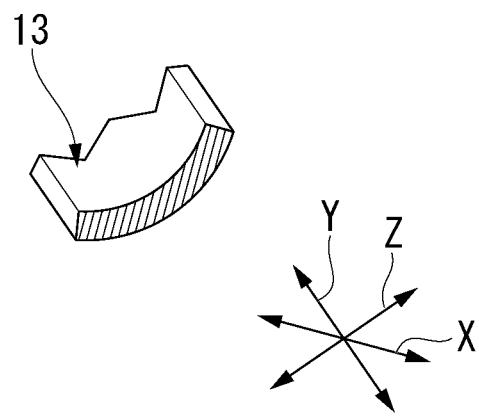
FIG. 4 is a schematic perspective view broken along a cutting line IV-IV shown in FIG. 3.

The first arm 12 and the second arm 13 are formed to have a rounded shape that a cross-sectional shape orthogonal to a longitudinal direction at the distal end side is an arc shape, as shown in FIG. 4. More specifically, a central portion on the outer surface of the first arm 12 and the second arm 13 in the orthogonal direction Z described below is formed in a curved surface shape as a convex portion outwardly.

The first arm 12 and the second arm 13 are configured in such a manner so as to have improved strength against bending and reduce frictional resistance to the outer sheath 50 described below so as to smoothly advance and retract.

As shown in FIG. 1A, an opposite direction X in which the first arm 12 and the second arm 13 face each other, an axial direction Y parallel to the axis C1 of the pressing tube 31, and an orthogonal direction Z that is orthogonal to each of the opposite direction X and the axial direction Y are defined. As shown in FIG. 2, two first locked portions 16, 17 are provided at the proximal end portion of the first arm 12. The first locked portions 16, 17 are provided on a reference plane S1 parallel to the axis line (central axis line) C1 of the pressing tube 31 so as to protrude from a lateral surface of the first arm 12 in the orthogonal direction Z. The first locked portions 16, 17 protrude in directions opposite to each other.

FIG. 2 is a view from a direction orthogonal to the reference plane S1. In the planar view shown in FIG. 2, the first locked portion 16 and the first locked portion 17 are line-symmetric with respect to the axis C1.

As shown in FIG. 2, a proximal end surface 16a of the first locked portion 16 is inclined to be separated from the first arm 12 (center axis line C1) toward the distal end side. A distal end surface 16b of the first locked portion 16 is orthogonal to the axial direction Y. A proximal end surface 17a of the first locked portion 17 and the proximal end surface 16a of the first locked portion 16 are line-symmetric with respect to the axis C1. The distal end surface 17b of the first locked portion 17 and the distal end surface 16b of the first locked portion 16 are line-symmetric with respect to the axis C1.

As shown in FIG. 1A and FIG. 2, in the first arm 12, two protrusions 18, 19 are provided at a more distal end side of the first locked portions 16, 17 of the first arm 12 respectively. The protrusions 18 and 19 protrude from a lateral surface of the first arm 12 in the orthogonal direction Z. The protrusion 18 and the protrusion 19 are line-symmetric with respect to the axis C1 in a planar view. Lengths of the protrusions 18, 19 protruding from the first arm 12 may be longer than the length of the first locked portions 16, 17 protruding from the first arm 12 in the orthogonal direction Z, respectively.

As shown in FIG. 1A, a claw 13a extending toward the first arm 12 side is formed at a distal end portion of the second arm 13.

Figure 5:
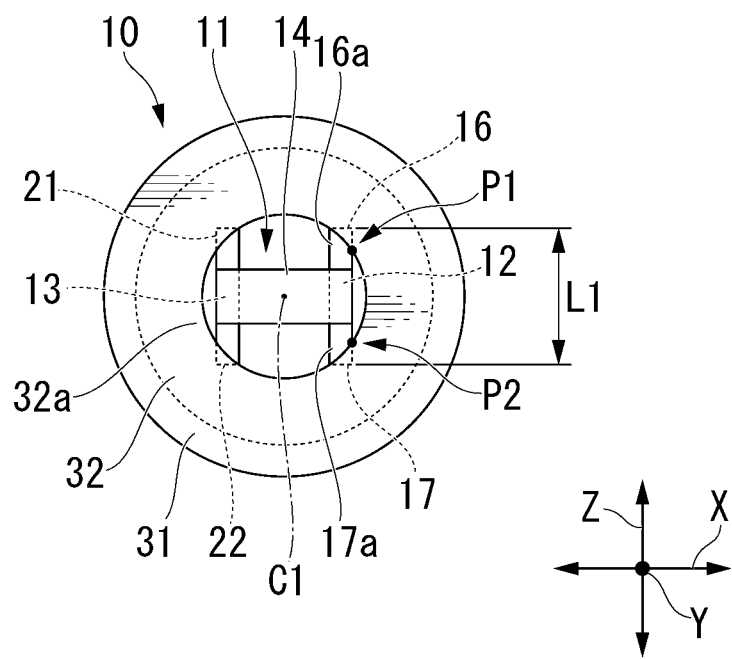
FIG. 5 is a view schematically showing a state of the endoscope clip in FIG. 1A viewed from the proximal end side.

Second locked portions 21, 22 and protrusions 23, 24 are formed in the second arm 13 similar to the first locked portions 16, 17 and the protrusions 18, 19 of the first arm 12 (the second locked portion 22 is shown in FIG. 5, and the protrusion 24 is not shown). In other words, the second locked portions 21, 22 of the second arm 13 protrude from the lateral surface of the second arm 13 in the orthogonal direction Z which is a direction in which the second arm 13 is separated from the first arm 12. The protrusions 23, 24 of the second arm 13 protrude in the orthogonal direction Z from the lateral surface of the second arm 13 at a more distal end side of the second locked portions 21, 22 of the second arm 13. The second locked portions 21, 22 and the protrusions 23, 24 are arranged in the opposition direction X with respect to the first locked portions 16, 17 and the protrusions 18, 19 respectively. In the planar view shown in FIG. 2, the second locked portions 21, 22 overlap the first locked portions 16, 17, and the protrusions 23, 24 overlap the protrusions 18, 19, respectively.

In the side view shown in FIG. 1A, the first arm 12 and the second arm 13 are formed at positions being line-symmetric with respect to the axis C1.

For example, the arm portion 11 is formed by punching a plate material formed of a cobalt chrome alloy into a shape as expanding the first arm 12, the second arm 13, the central portion 14, the first locked portions 16, 17, the second engaged portion 21, 22 and the protrusions 18, 19, 23, 24 into a flat shape. The arm portion 11 is integrally formed by being bent at a connecting portion between the first arm 12 and the central portion 14, and a connecting portion between the second arm 13 and the central portion 14 to form a C-shape in a side view.

The first arm 12 and the second arm 13 of the arm portion 11 have an elastic restoring force applied in a direction in which distal ends thereof are separated from each other, that is, a direction in which the arm portion 11 opens.

As shown in FIG. 2, the locking portion 32 are protruding over the whole circumference in the inner wall of the proximal end portion of the pressing tube 31. When viewed in the axial direction Y shown in FIG. 5, an edge portion 32a at the axis C1 side of the locking portion 32 is formed in a circular shape coaxial with the pressing tube 31. As shown in FIG. 2, a proximal end surface 32b (proximal end side end surface) and a distal end surface 32c (distal end side end surface) of the locking portion 32 are orthogonal to the axial direction Y.

A portion of the first arm 12 at the proximal end side more than the protrusions 18, 19, a portion of the second arm 13 at the proximal end side more than the protrusions 23, 24, and the central portion 14 are insertable into the locking portion 32. As shown in FIG. 5, a length L1 from an end of the first locked portion 16 to the first locked portion 17 is smaller than the inner diameter of the locking portion 32. In an initial state described below, when viewed from the axis direction Y, part of each of the first locked portions 16, 17 overlaps the locking portion 32. In other words, in the state shown in FIG. 5, the edge portion 32a is configured to face the first locked portions 16, 17 at the positions P1, P2, and the length L1 of the first locked portions 16, 17 is set to be larger than a height of the edge portion 32a at the positions P1, P2 in the orthogonal direction Z (a length of a line connecting the position P1 and the position P2 in FIG. 5).

As shown in FIG. 2, a tapered surface 31a is formed on the inner circumferential surface of the distal end portion of the pressing tube 31 over the whole circumference. The tapered surface 31a has a diameter that increases toward the distal end side.

The pressing tube 31 and the locking portion 32 are integrally formed of a material such as 64 titanium alloy (Ti-6AL-4V) or cobalt chromium alloy.

As shown in FIG. 2, an end turn portion 36b is provided at the distal end portion of the coil spring 36. The end turn portion 36b is formed to have an inner diameter smaller than that of the other portion of the coil spring 36.

In a state in which the coil spring 36 is accommodated in the pressing tube 31, a distal end portion thereof is locked by the protrusions 18, 19, 23, 24 and a proximal end portion thereof is locked by the locking portion 32. The proximal end portion of the coil spring 36 and the locking portion 32 may be fixed by welding or the like.

A portion of the first arm 12 at the proximal end more than the protrusions 18 and 19, a portion of the second arm 13 at the proximal end more than the protrusions 23 and 24, and the central portion 14 are insertable into the coil spring 36. When the protrusions 18, 19, 23, 24 move to the proximal end side, the protrusions 18, 19, 23, 24 are locked by the end turn portion 36b of the coil spring 36. On the other hand, when the protrusions 18, 19, 23, 24 move to the proximal end side, the coil spring 36 is compressed by the protrusions 18, 19, 23, 24 in the axis direction Y. When the coil spring 36 is compressed, an elastic force for pushing the arm portion 11 out from the pressing tube 31 is generated in the axis direction Y.

Even in a case in which the coil spring 36 does not include the end turn portion 36b, the same effect may be achieved by attaching another member such as a washer or the like to the distal end of the coil spring 36.

(Configuration of Treatment Tool Main Body 40)

Next, a configuration of the treatment tool main body 40 (applicator) will be described.

As shown in FIGS. 1A and 2, the treatment tool main body 40 includes an outer sheath 50, an insertion portion 60, and an operation portion (operator) 100. The insertion portion 60 is advanceable and retractable in the outer sheath 50. The operation portion 100 is attached to the proximal end of the insertion unit 60.

For example, the outer sheath 50 may be formed of a fluororesin such as PTFE (polytetrafluoroethylene) or a resin material such as HDPE (high density polyethylene).

The insertion portion 60 of the treatment tool main body 40 includes a sheath 61, an operation wire (wire) 62, and a connection member 63. The operation wire 62 is inserted into the sheath 61 to be advanceable and retractable. The connection member 63 is connected to the distal end portion of the operation wire 62. The connection member 63 is provided to be rotatable with respect to the operation wire 62 and with an axis parallel to the opposite direction X as a rotation center.

The sheath 61 has a coil sheath 66 and a distal member (stopper) 67 fixed to the distal end portion of the coil sheath 66. The coil sheath 66 is formed of stainless steel such as SUS301 or the like having high compression strength.

The coil sheath 66 may be configured by using a coil formed by closely winding strand wires in the axial direction Y which is not shown in figures. The coil sheath 66 has flexibility and is strong against a compressive force in the axial direction Y. An inner diameter of the coil sheath 66 is approximately the same as the inner diameter of the coil spring 36.

For example, the distal member 67 is formed of stainless steel in a cylindrical shape. The inner diameter of the distal member 67 is smaller than the inner diameter of the coil sheath 66. The outer diameter of the distal member 67 is larger than the outer diameter of the coil sheath 66 and the pressing tube 31E. On the outer circumferential surface of the proximal end portion of the distal member 67, a concave portion 67a is formed by reducing the outer diameter thereof. The distal member 67 and the coil sheath 66 are fixed by laser welding or the like with the distal end of the coil sheath 66 engaged with the concave portion 67a.

On the inner circumferential surface of the distal end portion of the sheath 61, a step portion 68 is formed in the connecting portion between the coil sheath 66 and the distal member 67 by reducing the inner diameter of the distal member 67 at the distal end side more than the coil sheath 66 with respect to the coil sheath 66. The inner diameter of the distal member 67 may be large such that the distal member 67 and the first locked portions 16, 17, the second locked portions 21, 22 do not engage with each other when the clip 10E described below is locked by the locking portion 32.

A step portion is formed on the inner circumferential surface of the distal end portion of the distal member 67 over the entire circumference. In the step portion, the surface facing the distal end side is the distal end support surface (distal end surface) 67b. A support portion 69 is formed at the distal end side more than the distal end support surface 67b. According to the present embodiment, the support portion 69 is formed in a cylindrical shape. The inner diameter of the support portion 69 is slightly larger than the outer diameter of the pressing tube 31E so as to be capable of receiving the proximal end of the pressing tube 31E. The distal end support surface 67b may contact the proximal end surface of the pressing tube 31E. A clip 10 is disposed at the distal end side of the sheath 61. The support portion 69 may support the outer circumferential surface of the pressing tube 31 that is in contact with the distal end support surface 67b.

According to these configurations, the unstableness of the clip 10 with respect to the support portion 69 may be suppressed as small as possible, and the inclination of the clip 10E with respect to the support portion 69 may be acceptable. Accordingly, the endoscope clip 1 may be smoothly inserted into the channel of the endoscope or the like even formed in a bent shape.

The operation wire 62 is made of, for example, a metal single wire or a twisted wire. The distal end of the operation wire 62 is connected to the proximal end of the enlarged diameter portion 72. A loop portion 73 and a hook 77 are connected to the distal end portion of the enlarged diameter portion 72.

The enlarged diameter portion 72 is formed of, for example, a metal material or the like in a cylindrical shape. The outer diameter of the enlarged diameter portion 72 is smaller than the inner diameters of the coil sheath 66 and larger than the inner diameter of the distal member 67. A length L2 (see FIG. 15) as a protrusion amount of the loop portion 73 with respect to the sheath 61 is restricted by the step portion 68 being contact to the distal end surface of the enlarged diameter portion 72. The length L2 is the maximum protrusion amount of the loop portion 73 allowed by the distal member 67.

The loop portion 73 is formed by folding back one wire 73a. The wire 73a has a folded-back portion located at the distal end side, and two ends at the proximal end side are fixed to the enlarged diameter portion 72 by brazing, resistance welding or the like.

As shown in FIG. 2, the connection member 63 is configured to have a hook 77 at the distal end portion of a connection portion maim body 76 and a penetration hole 76a formed in the proximal end portion of the connection portion maim body 76. An inclined surface 76b is formed on a surface in the connection portion maim body 76 opposite to the hook 77.

The connection member 63 is connected to the loop portion 73 to be rotatable (rotatable in the arrow direction D shown in FIG. 2) with respect to the loop portion 73 and with the axis parallel to the opposite direction X as the rotation center by inserting the folded-back portion of the wire 73a of the loop portion 73 into the penetration hole 76a.

A width of the connection member 63 is an outer diameter in a direction orthogonal to the central axis line C1 of the connection portion main body 76 when the hook 77 is disposed at the distal end side. The width of the connection member 63 is slightly smaller than the inner diameter of the coil spring 36, the inner diameter of the coil sheath 66, and the inner diameter of the distal member 67. That is, inside the pressing tube 31 and the sheath 61, the connection member 63 is not rotatable with respect to the loop portion 73 in the state in which the hook 77 is disposed at the distal end side. In other words, the relative movement in the radial direction of the arm portion 11 and the hook 77 is restricted by the pressing tube 31 and the sheath 61.

The above-mentioned recitation "the connection member 63 is not rotatable with respect to the loop portion 73" means that the connection member 63 is not rotatable with respect to the loop portion 73 until the engagement between the hook 77 and the central portion 14 is released. Accordingly, "the connection member 63 is not rotatable with respect to the loop portion 73" does not literally mean that the connection member 63 is totally not rotatable with respect to the loop portion 73.

The hook 77 may be engaged with the central portion 14 by disposing the central portion 14 between the hook 77 of the connection member 63 and the inclined surface 76b. When the hook 77 is rotated in the direction D with respect to the loop portion 73 (see FIG. 2), the engagement between the hook 77 and the central portion 14 is released (see FIG. 16). In this manner, the connection member 63 is detachably connected to the arm portion 11. The connection member 63 is positioned in the pressing tube 31.

As shown in FIG. 1A, the operation portion 100 has an operation portion main body (handle) 101, a slider 102, and a limiter (limiting portion) 64.

The operation portion main body 101 is attached to the proximal end portion of the coil sheath 66. The operation portion main body 101 is formed in a rod shape extending in the axial direction Y, and has a finger hook portion 101a at the proximal end portion. A slit 101b extending in the axial direction Y is formed in the operation portion main body 101.

The slider 102 is outwardly fitted to the operation portion main body 101. The slider 102 is slidable (advance and retract) in the axial direction Y with respect to the operation portion main body 101. The proximal end of the operation wire 62 is connected to the distal end portion of the slider 102. In the clip 10 according to the present embodiment, the operation wire 62 is advanced or retracted by operating the slider 102 to advance or retract in the axial direction Y. The enlarged diameter portion 72, the loop portion 73, the hook 77, and the arm portion 11 of the clip 10 disposed on the distal end side of the operation wire 62 may be advanceable or retractable. As a result, the pair of first arm 12 and second arm 13 of the arm portion 11 may be opened or closed.

The slider 102 is formed in a cylindrical shape. On the outer circumferential surface of the slider 102, a recess portion 102a is formed over the entire circumference. In the slider 102, a flange portion 102b, the recess portion 102a, and a flange portion 102c are formed in this sequence from the distal end side toward the proximal end side in the axial direction Y. The pair of flange portions 102b and 102c are formed in an elliptical shape when viewed in the axial direction Y. As a result, the slider 102 is easy to be grasped, and space may be saved when the operation portion 100 of the endoscope clip 1 is packaged.

The movement range of the slider 102 with respect to the operation portion main body 101 in the axial direction Y is restricted by the slider 102 engaging with the slit 101b of the operation portion main body 101.

The limiter 64 is a hollow tubular member formed to extend along the axial direction Y of the slider 102. As shown in FIG. 1B, the limiter 64 has an inner cavity 641 through which the operation wire 62 is insertable. The limiter 64 is formed of, for example, a resin material. The limiter 64 has a rigidity such that the limiter 64 is not compressed even if a predetermined pressure in the longitudinal axis direction is applied thereto. The dimension of the limiter 64 in the longitudinal axis direction is not particularly limited. For example, the dimension of the limiter 64 in the longitudinal axis direction only has to be equal to or smaller than the value achieved by subtracting the dimension of the slider 102 in the longitudinal axis from the dimension of the slit 101b of the operation portion main body 101 in the longitudinal axis direction.

However, as described below, since there is a correlation between the dimension of the limiter 64 in the longitudinal axis direction and the opening width of the arm portion 11, it is preferable to determine the dimension of the limiter 64 in the longitudinal axis by taking the desired opening width of the arm portion 11 into consideration.

As shown in FIG. 1B, in a cross-sectional view of the slider 102 along the axial direction Y, a shape of the cross section of the limiter 64 according to the present embodiment is a substantially C-shape. The limiter 64 has a slit portion 642 formed to connect the inner cavity 641 and the outside. The slit portion 642 is an elongated notch formed to extend along the axial direction Y of the slider 102. The slit portion 642 has an opening width slightly smaller than the diameter of the operation wire 62. The slit portion 642 is deformable such that when the operator removes the limiter 64, the slit portion 642 is deformed to form a gap having a size suitable for the operation wire 62 to pass through.

According to the present embodiment, as shown in FIG. 1A, the limiter 64 is disposed in the slit 101b of the operation portion main body 101 while covering the operation wire 62. The limiter 64 is disposed at the distal end side more than the slider 102 in the slit 101b. At this time, the movable range of the slider 102 refers to a range by subtracting the dimension of the limiter 64 in the longitudinal axis direction from the length of the slit 101b of the operation portion main body 101 from the proximal end of the slit 101b toward the distal end side. In other words, the limiter 64 according to the present embodiment is a member configured to limit the pushing amount of the operation wire 62.

Figure 17:
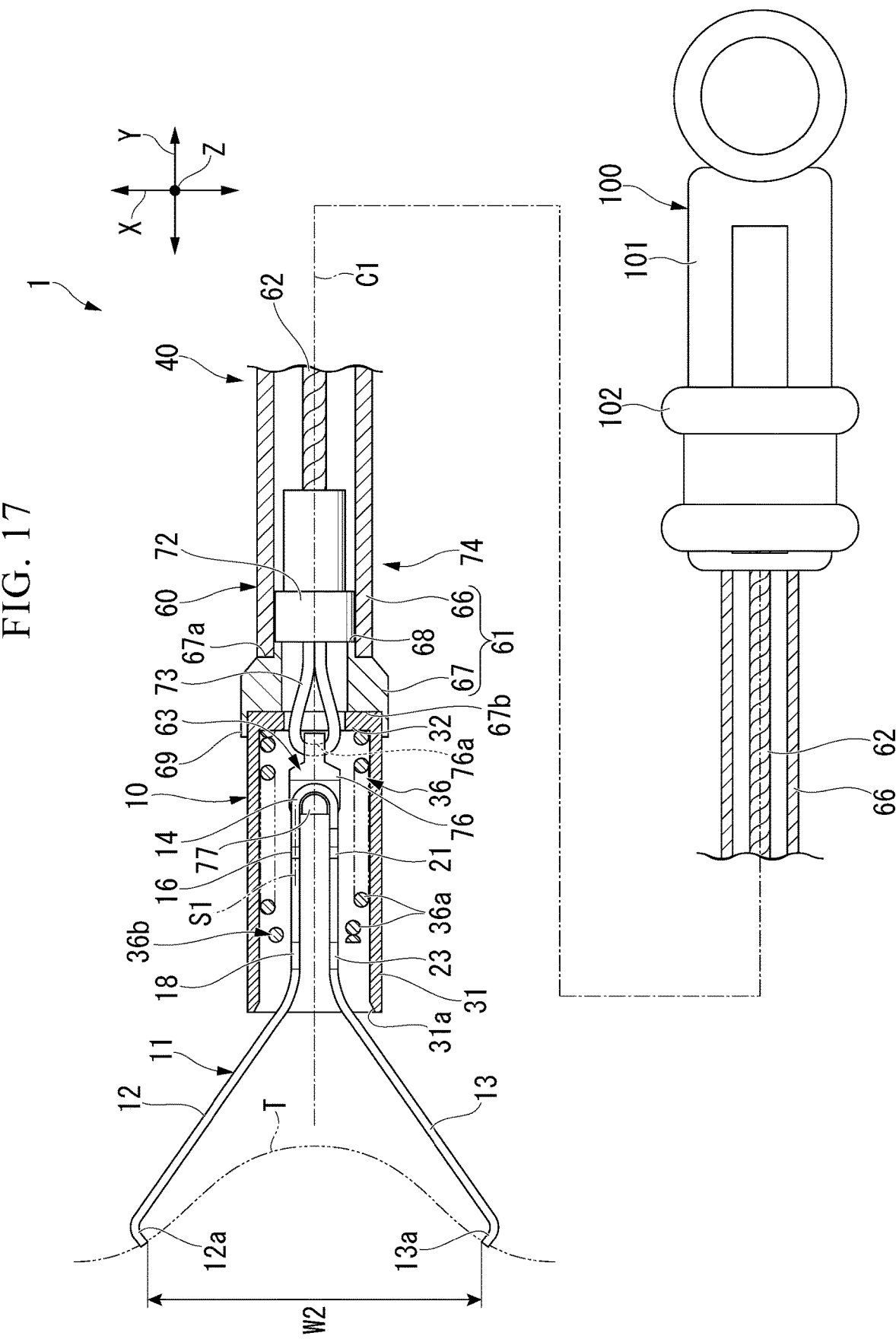
FIG. 17 is a cross-sectional view schematically showing broken part of the lateral surface of the endoscope clip in a state in which the limiter of the endoscope clip according to the present embodiment is removed.
Figure 18:
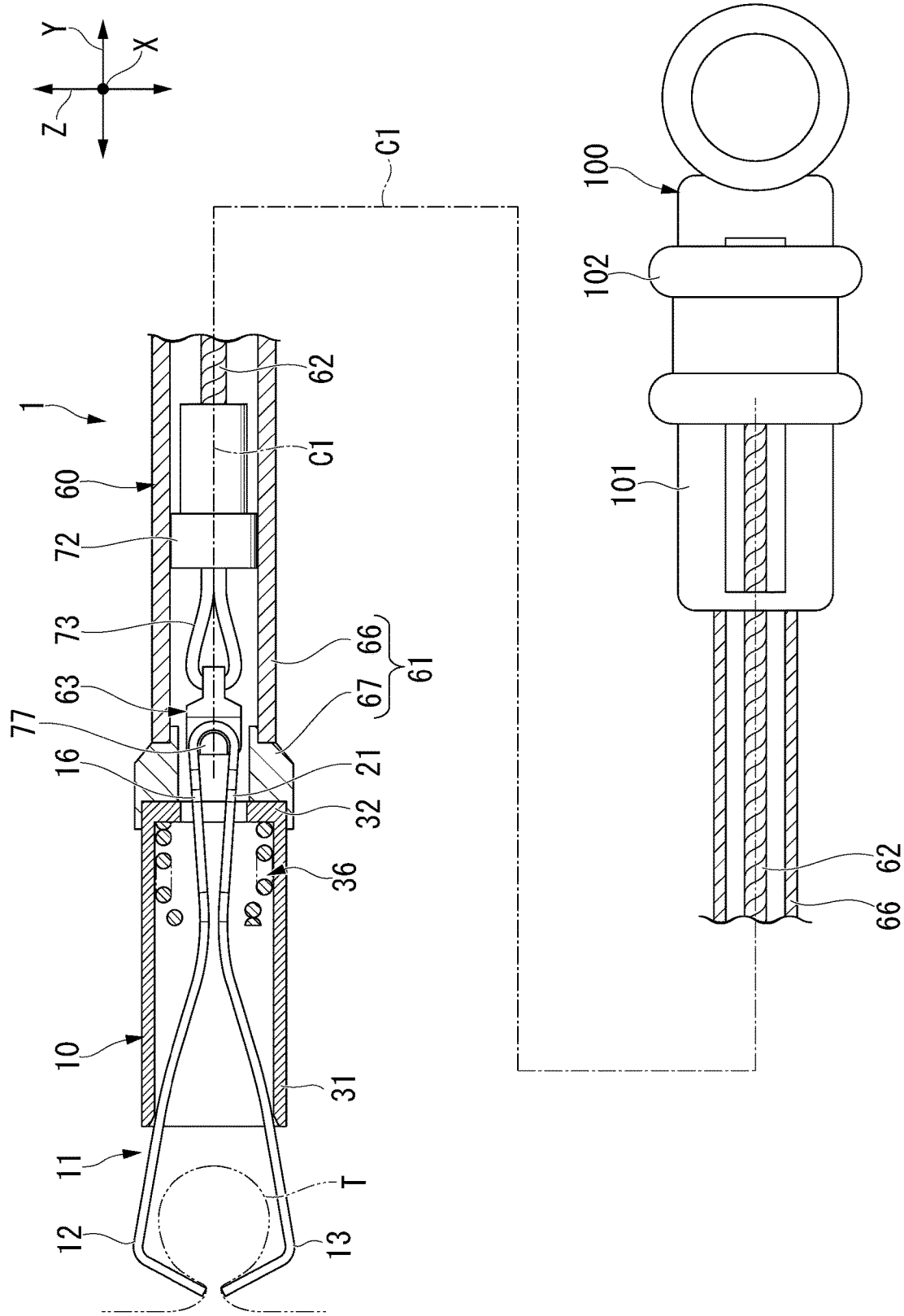
FIG. 18 is a cross-sectional view schematically showing the locking state of the endoscope clip in the state in which the limiter of the endoscope clip according to the present embodiment is removed.
Figure 19:
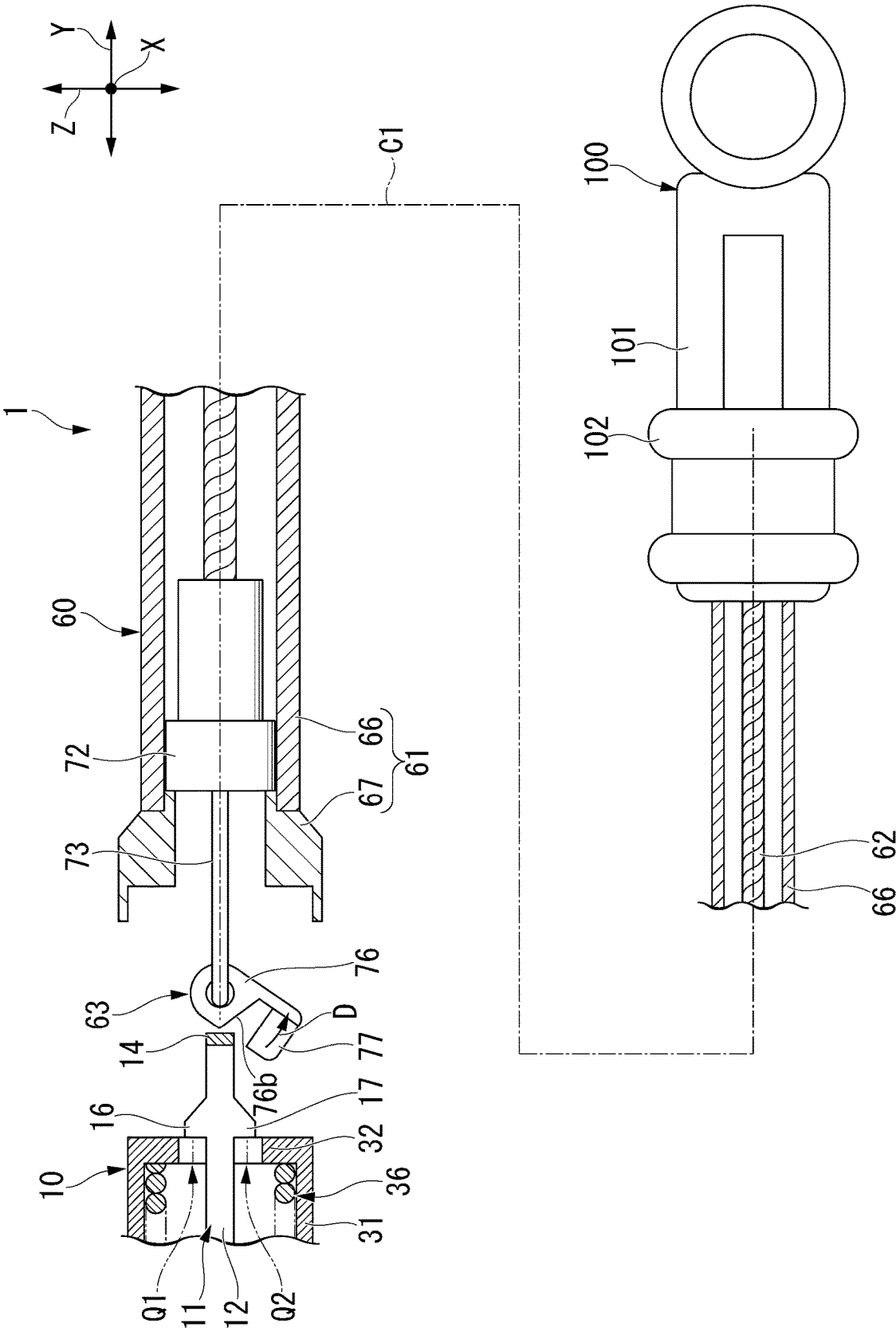
FIG. 19 is a view schematically showing the procedures of indwelling the endoscope clip in the body in the state in which the limiter of the endoscope clip according to the present embodiment is removed.

On the other hand, as shown in FIGS. 17-19, when the limiter 64 is removed, the movable range of the slider 102 is within the range of the whole length of the slit 101b of the operation portion main body 101 in the longitudinal axis direction.

(Initial State of Endoscope Clip 1)

Next, a medical procedure for ligating the target tissue T using the endoscope clip 1 having the above-described configuration will be described.

Figure 6:
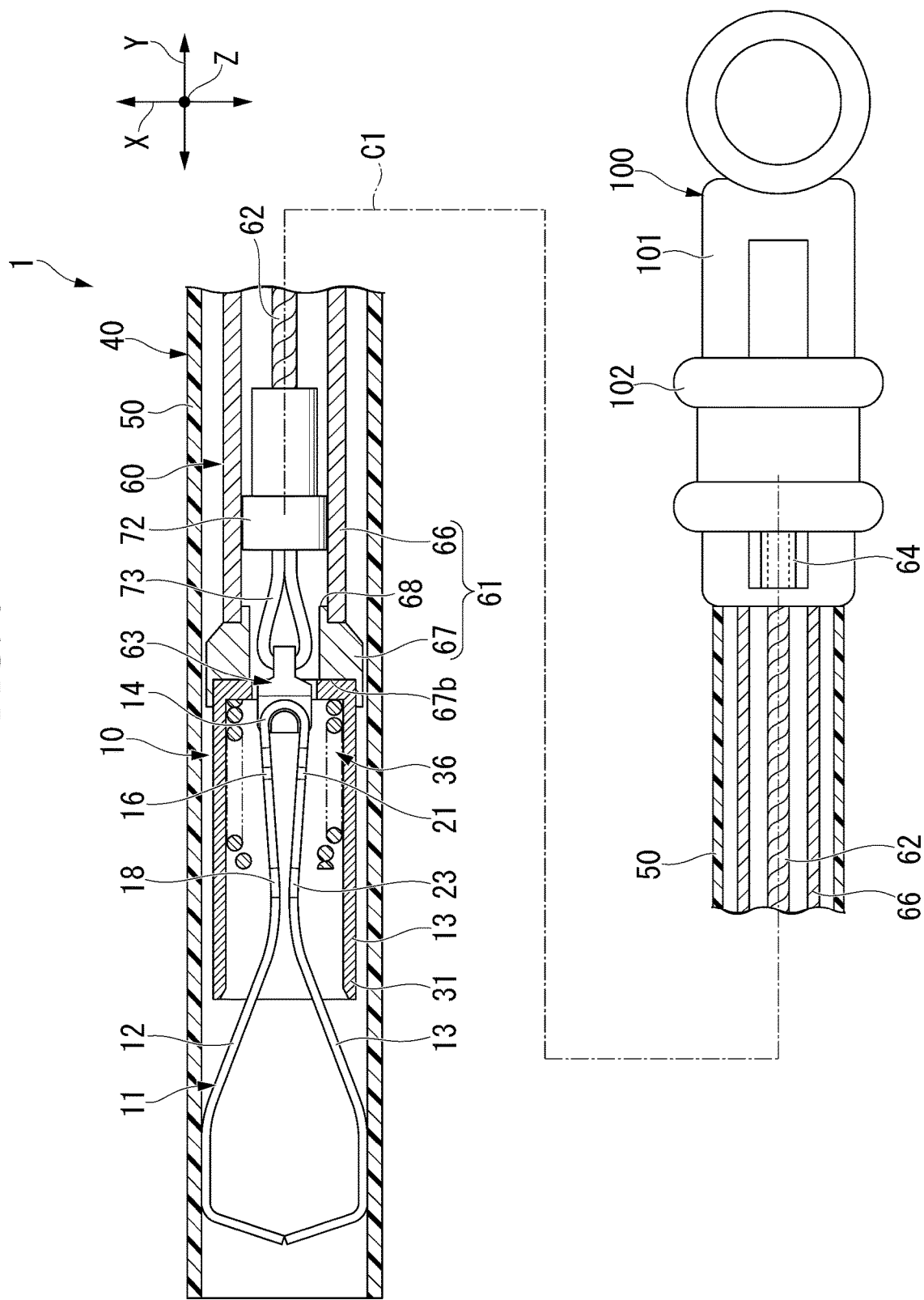
FIG. 6 is a cross-sectional side view schematically showing an initial state of the endoscope clip according to the present embodiment.

In the initial state before the procedure is started, when the endoscope clip 1 is provided to the operator as a surgery, as shown in FIG. 6, the clip 10 is in the state of being attached to the treatment tool main body 40 and covered by the outer sheath 50.

As shown in FIG. 6, in the initial state, the coil spring 36 of the clip 10 is slightly compressed in the axis direction Y than the nature state (the state in which there is no external force applied) and the strand wires 36a being adjacent to each other in the axis direction Y are separated from each other. The proximal end surface of the pressing tube is in contact with the distal end support surface 67b. On the other hand, the distal end surface of the slider 102 in the operation portion 100 at the proximal end side is in contact with the proximal end surface of the limiter 64 such that the movable range of the slider 102 toward the distal end side is limited by the limiter 64. As a result, the enlarged diameter portion 72 is positioned at the proximal end side than the step portion 68 in the coil sheath 66 of the insertion portion 60, and the enlarge diameter portion 72 and the step portion 68 are separated from each other. The connection member 63 is disposed inside the pressing tube 31 such that the connection is not rotatable with respect to the loop portion 73 and the engagement of the hook 77 and the central portion 14 is maintained.

In the initial state, as shown in FIG. 6, the proximal end portion of the first arm 12, the proximal end portion of the second arm 13, and the central portion 14 are positioned at the distal end side more than the locking portion 32 in the pressing tube 31. When the stopper 72 abuts the fixing member 74, the first engaged portions 16, 17 and the second engaged portions 21, 22 of the arm portion 11 are located on the distal end side more than the locking portion 32. At this time, the first locked portions 16, 17 and the second locked portions 21, 22 are not in contact with the locking portion 32 of the pressing tube 31. A portion between the distal end and the proximal end each of the first arm 12 and the second arm 13 of the arm portion 11 is in contact with the inner wall of the outer sheath 50. The first arm 12 and the second arm 13 of the arm portion 11 are spaced apart from the inner wall of the outer sheath 50 with a space therebetween. In the arm portion 11, the distal end of the first arm 12 and the distal end of the second arm 13 are in contact with each other (or a distance between the distal end of the first arm 12 and the distal end of the second arm 13 is substantially zero). In the present description, both the state in which the distal end of the first arm 12 and the distal end of the second arm 13 are in contact with each other and the state in which the distance between the distal end of the first arm 12 and the distal end of the second arm 13 is substantially zero are regarded as the state in which the first arm 12 and the second arm 13 are closed and defined as a closed configuration of the clip 10. According to the present embodiment, for example, the state in which the distance between the distal end of the first arm 12 and the distal end of the second arm 13 is substantially zero may be a state when the target tissue T is tightly bound by the first arm 12 and the second arm 13 at the root thereof.

In the initial state, the slider 102 is in contact with the limiter 64 in the slit 101b of the operation portion main body 101. The limiter 64 is in contact with the distal end surface 101d of the slit 101b of the operation portion main body 101.

In the initial state, the orientation or posture of the clip 10 may be adjusted by rotating the operation wire 62 with respect to the sheath 61. At this time, it is considerable that the arm portion 11 rotates around the axis C1 with respect to the pressing tube 31. However, the edge portion 32a of the locking portion 32 is formed in the circular shape and coaxial with the pressing tube 31 such that the engagement between the locking portion 32 and the first locked portions 16, 17 and the second locked portions 21, 22 is suitably maintained.

When using the endoscope clip 1, the operator inserts an endoscope (not shown) into the body of the patient. Subsequently, the operator inserts the outer sheath 50 of the endoscope clip 1 from the proximal end portion of the channel of the endoscope, and protrudes the outer sheath 50 from the distal end portion of the channel of the endoscope.

Next, the operator operates the operation portion main body 101 to pull back the outer sheath 50 with respect to the insertion portion 60 of the treatment tool main body 40 so as to release the state in which the first arm 12 and the second arm 13 of the clip 10 are in contact with the inner circumferential surface of the outer sheath 50.

As described above, the arm portion 11 of the clip 10 according to the present embodiment has an elastic restoring force in the direction in which the distal ends of the first arm 12 and the second arm 13 move to be separated from each other. Accordingly, the opening width of the first arm 12 and the second arm 13 increases while the first arm 12 and the second arm 13 are in contact with the tapered surface 31a provided on the inner circumferential surface of the distal end portion of the pressing tube 31 such that the first arm 12 and the second arm 13 enter the open state. As a result, due to the elastic restoring force of the first arm 12 and the second arm 13, the arm portion 11 is biased toward the direction in which the arm portion 11 protrudes from the pressing tube 31. That is, the elastic restoring force of the first arm 12 and the second arm 13 functions to move the arm portion 11 toward the distal end side.

In this state, as shown in FIG. 1A, the first arm 12 and the second arm 13 are in contact with the tapered surface 31a of the distal end portion of the pressing tube 31. As described below, the opening width between the first arm 12 and the second arm 13 is restricted by the tapered surface 31a of the distal end portion of the pressing tube 31 and the opening width is smaller than the maximum opening width.

When the distal end surface of the slider 102 comes in contact with the proximal end surface of the limiter 64, the slider 102 is impossible to further move with respect to the operation portion main body 101 due to the limiter 64. The position (the position of the slider 102 shown in FIG. 1A) where the slider 102 advances to the most distal end side with respect to the operation portion main body 101 and is in contact with the limiter 64 is defined as a neutral position. When the slider 102 is at the neutral position, as shown in FIG. 1A, the limiter 64 is sandwiched between the distal end surface of the slider 102 and the distal end surface 101d of the slit 101b of the operation portion main body 101.

When the slider 102 is at the neutral position, both the operation wire 62 connected to the slider 102 and the arm portion 11 connected to the operation wire 62 are in a state in which they are not advanceable with respect to the operation portion main body 101. Accordingly, as shown in FIG. 1A, the first arm 12 and the second arm 13 of the arm portion 11 are in a half-opened state (first open configuration) rather than a completely opened state. According to the present embodiment, the state in which the first arm 12 and the second arm 13 of the arm portion 11 are in the half-opened state is described as an example of the first open configuration; however, the first open configuration is not limited thereto.

In the first open configuration of the arm portion 11, the opening width of the half-opened arm portion 11 is defined as a first distance W1 between the first arm 12 and the second arm 13. In order to reliably grasp the target tissue T, the first distance W1 only has to be equal to or larger than the size of the target tissue T. However, taking the efficiency of the operator operating the endoscope clip 1 into consideration, the first distance W1 may be substantially equal to the size of the target tissue T.

Figure 7:
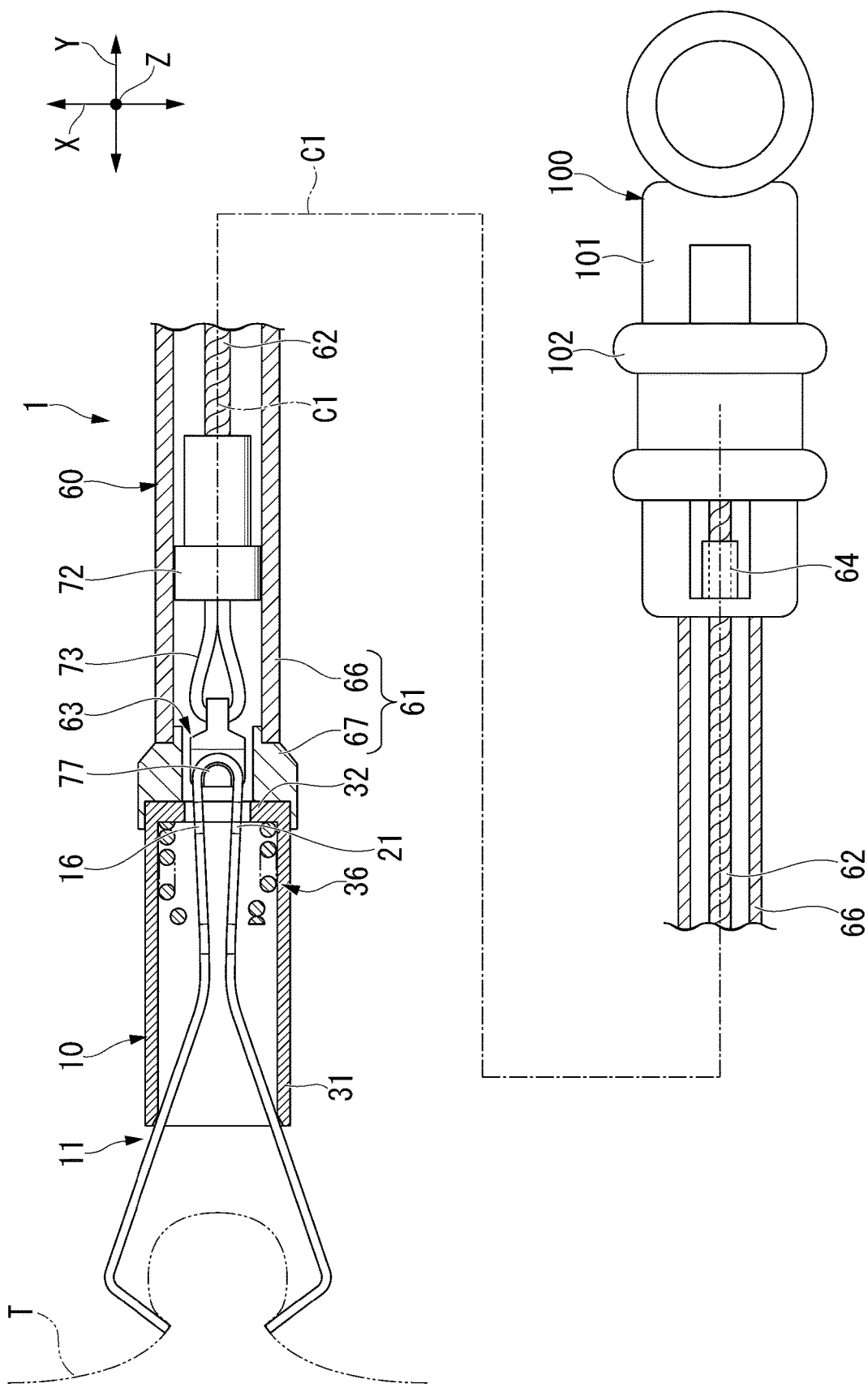
FIG. 7 is a cross-sectional side view schematically showing a contact state of the endoscope clip according to the present embodiment.

As shown in FIG. 7, the operator may position the target tissue T between the first arm 12 and the second arm 13 in the half-opened state. When the operator confirms that the target tissue T is located between the first arm 12 and the second arm 13, the operator may operate the endoscope to push the arm portion 11 toward the target tissue T so as to grasp the target tissue T.

In a case in which the distance between the first arm 12 and the second arm 13 is smaller than the size of the target tissue T, it is necessary to enlarge the opening width of the arm portion 11. At this time, the operator may further enlarge the opening width of the arm portion 11 by removing the limiter 64 from the slit 101b of the operation portion main body 101. In other words, when the operator removes the limiter 64, the movable range of the slider 102 may cover the whole length of the slit 101b of the operation portion main body 101 in the longitudinal axis direction.

In this state, the operator may further push the slider 102 toward the distal end side.

In the state in which the limiter 64 is removed, the operator further pushes the slider 102 toward the distal end side with respect to the operation portion main body 101 such that the first arm 12 and the second arm 13 of the arm portion 11 moves toward the distal end side. As a result, the opening width between the first arm and the second arm further increases while the first arm 12 and the second arm 13 are in contact with the tapered surface 31a at the distal end side of the pressing tube. As shown in FIG. 17, when the operator advances the slider 102 until the slider 102 comes in contact with the distal end surface of the slit 101b of the operation portion main body 101, the first arm 12 and the second arm 13 of the arm portion 11 are almost in a state of protruding from the pressing tube 31. In this state, the first arm 12 and the second arm 13 of the arm portion 11 are not restrained by the tapered surface 31a at the distal end side of the pressing tube 31 such that the opening width of the arm portion 11 becomes the maximum value. In the state in which the limiter 64 is detached, the operation to further push the slider 102 toward the distal end side with respect to the operation portion main body 101 is described; however, since the arm portion 11 is biased in the direction of protruding from the pressing tube 31 by the elastic restoring force of the first arm 12 and the second arm 13 and the elastic force by the coil spring 36, the arm portion 11 may move toward the distal end side with respect to the pressing tube 31 due to the biasing force. At this time, it is not necessary for the operator to push the slider 102.

As shown in FIG. 17, the state in which the opening width of the arm portion 11 is the maximum value is defined as a second open configuration of the arm portion 11. A distance between the distal end of the first arm 12 and the distal end of the second arm 13 in the second open configuration is defined as a second distance W2. The second distance W2 is larger than the first distance W1 described above. According to this embodiment, for example, the second distance W2 may be approximately twice the first distance W1.

In other words, according to the present embodiment, the arm portion 11 is restricted from being transitioned from the first open configuration to the second open configuration by the slider 102 and the limiter 64 engaging with each other.

(Contact State of Endoscope Clip 1)

When the operator confirms that the target tissue T is located between the first arm 12 and the second arm 13, the operator may grasp the operation portion main body 101 and pull back the slider 102. At this time, the slider 102 is not in contact with the limiter 64 and retreats toward the proximal end side along the slit 101b of the operation portion main body 101. At this time, the first arm 12 and the second arm 13 of the arm portion 11 move to the proximal end side while coming into contact with the tapered surface (inner circumferential surface) 31a at the distal end portion of the pressing tube 31. In such a state, the first arm 12 is elastically deformed toward the second arm 13 side, and the second arm 13 is elastically deformed toward the first arm 12 side. As a result, the distal end of the first arm 12 and the distal end of the second arm 13 approach each other, and the opening width of the arm portion 11 is decreased. That is, with the target tissue T positioned between the first arm 12 and the second arm 13, the arm portion 11 is transitioned from the first open configuration or the second open configuration to the closed configuration. At this time, the target tissue T is grasped by the first arm 12 and the second arm 13. According to the present embodiment, the state in which the target tissue is tightly bound by the first arm 12 and the second arm 13 at the root thereof and the distance between the first arm 12 and the second arm 13 is substantially zero is included in the closed configuration of the arm portion 11. In this manner, when the arm portion is transitioned from the first open configuration or the second configuration to the closed configuration, the coil spring 36 is compressed in the axis direction Y.

Figure 8:
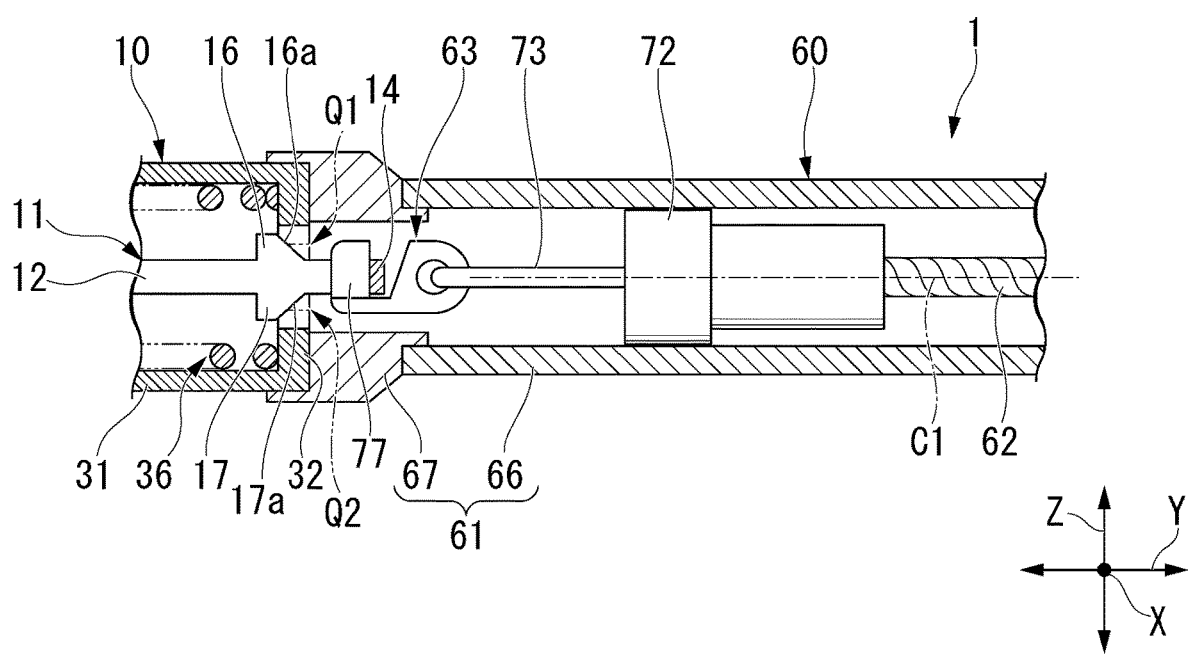
FIG. 8 is a cross-sectional planar view schematically showing the contact state of the endoscope clip according to the present embodiment.

When the operator grasps the operation portion main body 101 to further pulls back the slider 102, the first locked portions 16, 17 and the second locked portions 21, 22 are in contact with the locking portion 32 of the pressing tube 31. During this process, firstly, as shown in FIG. 5, the proximal end in the proximal end surface 16a of the first locked portion 16 comes in point contact with the edge portion 32a of the pressing tube 31 at the position P1, and the proximal end in the proximal end surface 17a of the first locked portion 17 comes in point contact with the edge portion 32a of the pressing tube 31 at the position P2. At this time, as shown in FIG. 7 and FIG. 8, the first locked portion 16 and the first locked portion 17 are in contact with the edge portion 32a of the pressing tube 31. The positions of the edge portion 32a in the orthogonal direction Z corresponding to the positions P1, P2 are shown as the positions Q1, Q2 in FIG. 2.

During the process of pulling back the slider 102, the coil spring 36 is compressed by the protrusion 18 and the protrusion 19 in the axis direction Y. During the process, when the distance at which the slider 102 is pulled back to the proximal end side, the compressed degree of the coil spring 36 is also increased such that the necessary force for the operator to pull back the slider 102 gradually increases.

The connection member 63 of the treatment tool main body 40 is disposed in the pressing tube 31 or the sheath 61 such that the connection member 63 does not rotate with respect to the loop portion 73 and the engagement of the hook 77 and the central portion 14 is maintained.

During the process of pulling back the slider 102 until entering the contact state, when the operator pushes the slider 102 toward the distal end side, the compressed coil spring 36 is extended. In the state in which the pressing tube 31 is in contact with the distal end support surface 67b, the arm portion 11 moves toward the distal end side with respect to the pressing tube 11. As a result, the operator may cause the first arm 12 and the second arm 13 of the arm portion 11 to be transitioned from the closed configuration to the above-described first open configuration or the second open configuration. Accordingly, the operator may operate the endoscope to direct the clip 10 toward the target tissue T again. The operator may grasp the target tissue T again following the above-described procedures.

(Climb-on State of Endoscope Clip 1)

Figure 9:
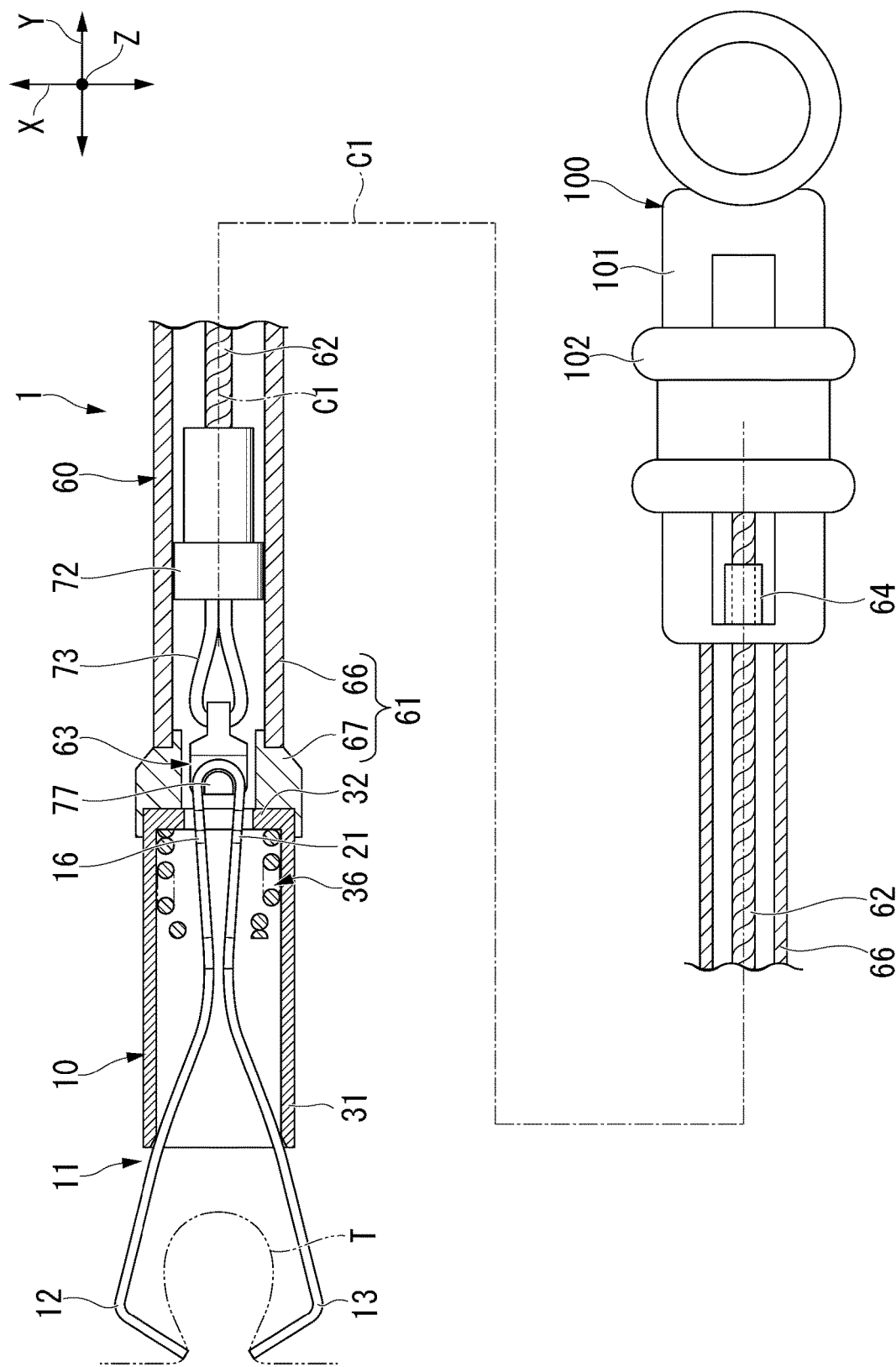
FIG. 9 is a cross-sectional side view schematically showing a climb-on state of the endoscope clip according to the present embodiment.
Figure 10:
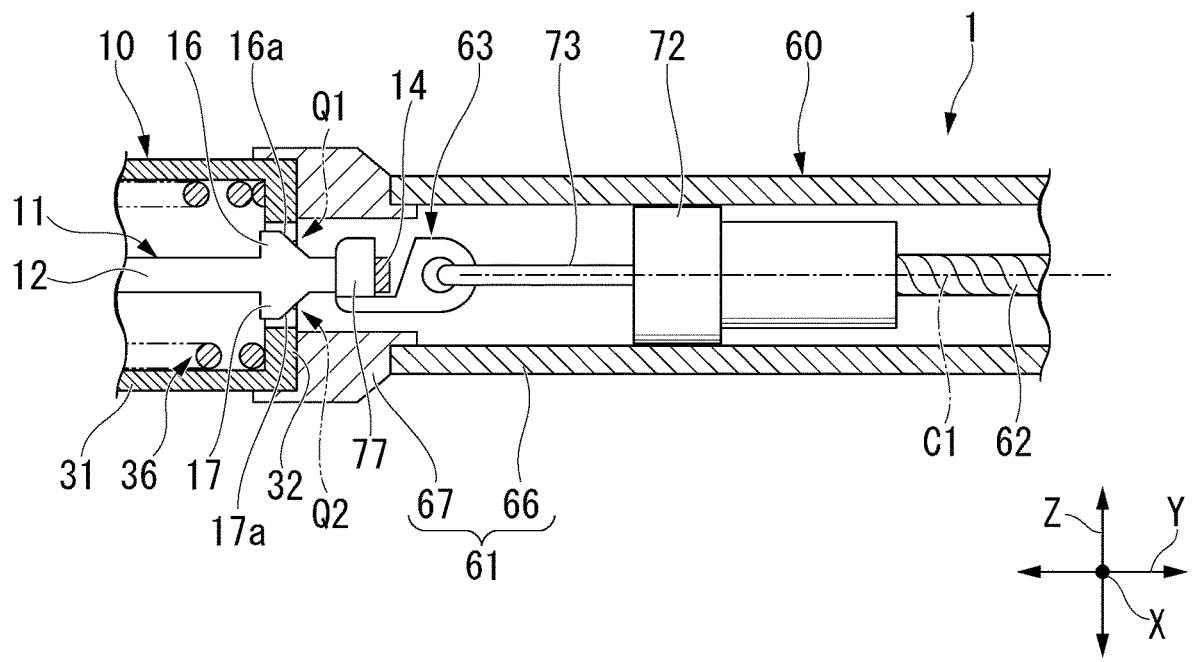
FIG. 10 is a cross-sectional planar view schematically showing the climb-on state of the endoscope clip according to the present embodiment.

When the operator further pulls back the slider 102 from the above-described contact state, the first arm 12 and the second arm 13 of the arm portion 11 further moves to the proximal end side. At this time, the first arm 12 and the second arm 13 are elastically deformed in a direction of approaching each other and pass through the locking portion 32. More specifically, as shown in FIG. 9 to FIG. 10, the first locked portions 16, 17 of the first arm 12 pass through the locking portion 32 in the elastically deformed state. At this time, the first locked portion 16 and the locking portion 32 are in the point contact state while the edge portion 32a of the locking portion 32 being in contact with the first locked portion 16 moves from the position P1 to the position P3. At the same time, the first locked portion 17 and the locking portion 32 are in the point contact state while the edge portion 32a of the locking portion 32 being in contact with the first locked portion 17 moves from the position P2 to the position P4.

Figure 11:
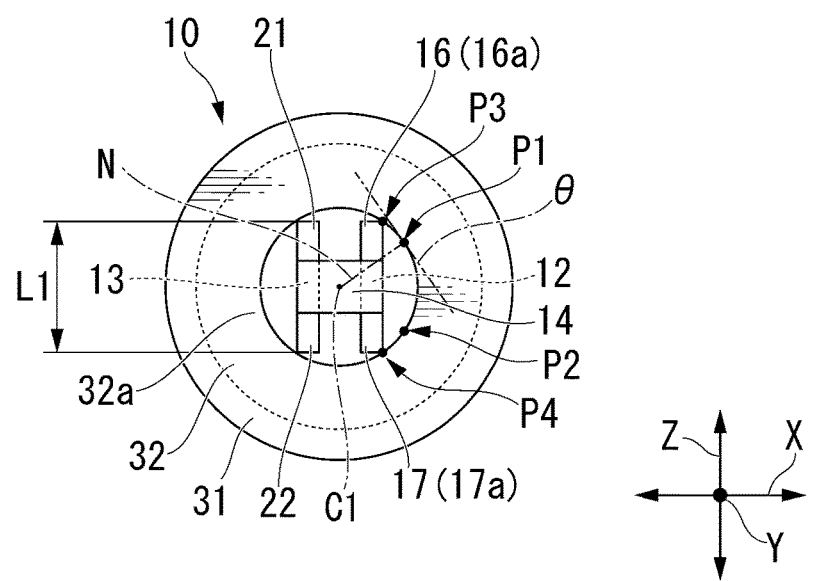
FIG. 11 is a view schematically showing a state of the endoscope clip in FIG. 9 viewed from the proximal end side.

The proximal end surfaces 16a, 17a of the first locked portions 16, 17 are inclined as described above, and the edge portion 32a is in a circular shape. Accordingly, when the slider 102 is pulled back, when viewed in the axis direction Y as shown in FIG. 11, the first locked portion 16 receives a normal resistance force from the edge portion 32 parallel to a normal line N orthogonal to a tangential line θ of the edge portion 32a at the position P1 at the edge portion 32a of the locking portion 32 where the first locked portion 16 and the edge portion 32a are in contact. Due to the normal resistance force, the first locked portion 16 of the first arm 12 moves in the opposite direction X approaching the second arm 13. At this time, the central portion 14 of the arm portion 11 is elastically deformed and two end portions of the central portion 14 itself move toward the axis C1 side.

As a result, as shown in FIG. 11, when viewed from the proximal end side of the clip 10, both the distal end portion of the proximal end surface 16a of the first locked portion 16 and the distal end portion of the proximal end surface 17a of the first locked portion 17 comes in contact with the edge portion 32a of the locking portion 32. The arm portion 11 enters the climb-on state in which the first locked portions 16, 17 and the second locked portions 21, 22 climb on and overcome the locking portion 32. At this time, the closed configuration of the first arm 12 and the second arm 13 of the arm portion 11 is maintained. As shown in FIG. 11, in the climb-on state, the distance between the position P3 and the position P4 of the edge portion 32a is equal to the length L1 of the first locked portions 16, 17.

During the process when the operator pulls back the slider 102 to the proximal end side and reaches the climb-on state of the arm portion 11, similar to the above-described disclosure, when the operator pushes the slider 102 toward the distal end side so as to move the arm portion 11 toward the distal end side. Accordingly, it is possible to cause the first arm 12 and the second arm 13 of the arm portion 11 to be transitioned from the first open configuration to the second open configuration. That is, the target tissue T may be grasped again until the arm portion 11 reaches the climb-on state.

During the process in which the operator pulls the slider 102 back toward the proximal end side and the first engaged portions 16, 17 climbs on and overcomes the engaging portion 32, compared to the process from the above-described initial state to the contact state, an increase rate of the necessary force for the operator to pulling the slider 102 per unit movement amount increases. That is, the operator feels heavy when pulling back the slider 102 from the contact state to the climb-on state. Accordingly, the operator may easily recognize a state in which the slider 102 is currently pulled back.

In the process in which the operator pulls back the slider 102 to the proximal end side and the arm portion 11 is transitioned from the contact state to the climb-on state, the connection member 63 is arranged inside the sheath 61 such that the engagement of the hook 77 and the central portion 14 is maintained. The necessary amount of force for changing the arm portion 11 from the contact state to the climb-on state is about 20 to 50 N (Newton), for example.

When the first engaged portions 16, 17 and the second engaged portions 21, 22 move to the proximal end side beyond the engaging portion 32, the first engaged portions 16, 17 and the second locked portion may climb on and overcome the engaging portion 32 by scraping the engaging portion 32 or cause the engaging portion 32 to be deformed. In such a case, in order to prevent the excessive destruction to the engaging portion 32, it is preferable to perform chamfering process to the portion of the first engaged portions 16, 17 and the second engaged portions 21, 22 contacting with the engaging portion 32.

(Locking State of Endoscope Clip 1)

When the operator further pulls back the slider 102 from the above-mentioned climb-on state, the first engaged portions 16, 17 and the second engaged portions 21, 22 move beyond the engaging portion 32 and further move toward the proximal end side. Both the configuration of the first arm 12 at the distal end side of the first engaged portions 16, 17 and the configuration of the second arm 13 at the distal side of the second engaged portions 21, 22 sequentially pass through the engaging portion 32. In the process, the positions of the first arm 12 and the second arm 13 in the opposite direction X and the orthogonal direction Z with respect to the pressing tube 31 are maintained.

At this time, the first arm 12, the second arm 13, and the central portion 14 are not biased by the engaging portion 32. Accordingly, due to the elastic force of the central portion 14, the proximal end side of the first arm 12 and the proximal end side of the second arm 13 move in the opposite direction X to be separated from each other.

When the operating force for moving the arm portion 11 to the proximal end side of the pressing tube 31 is released, the distal end surfaces 16b, 17b of the first engaged portions 16, 17 are in a state (locking state) of being locked to the proximal end surface 32b of the engaging portion 32.

In the process when the operator pulls back the slider 102 from the above-described climb-on state to the locking state, the first arm 12, the second arm 13, and the central portion 14 are no longer locked by the engaging portion 32, and the elastically deformation in these configurations are partially released. Accordingly, in the process from the climb-on state to the locking state, the necessary amount of force for the operator to pull back the slider 102 gradually decreases.

In the process when the operator pulls back the slider 102 from the above-described climb-on state to the locking state, the clip 10 is maintained in the closed configuration. Since the connection member 63 is arranged inside the sheath 61, the engagement between the hook 77 and the central portion 14 is maintained.

Figure 12:
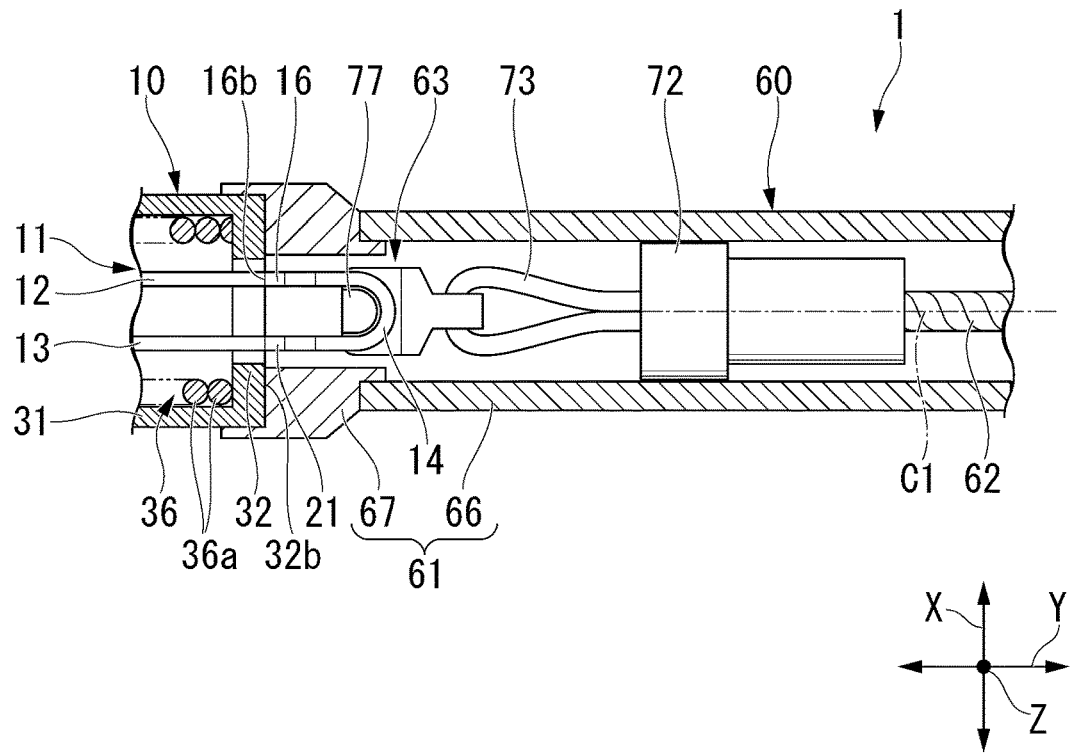
FIG. 12 is a cross-sectional side view schematically showing a locking state of the endoscope clip according to the present embodiment.
Figure 13:
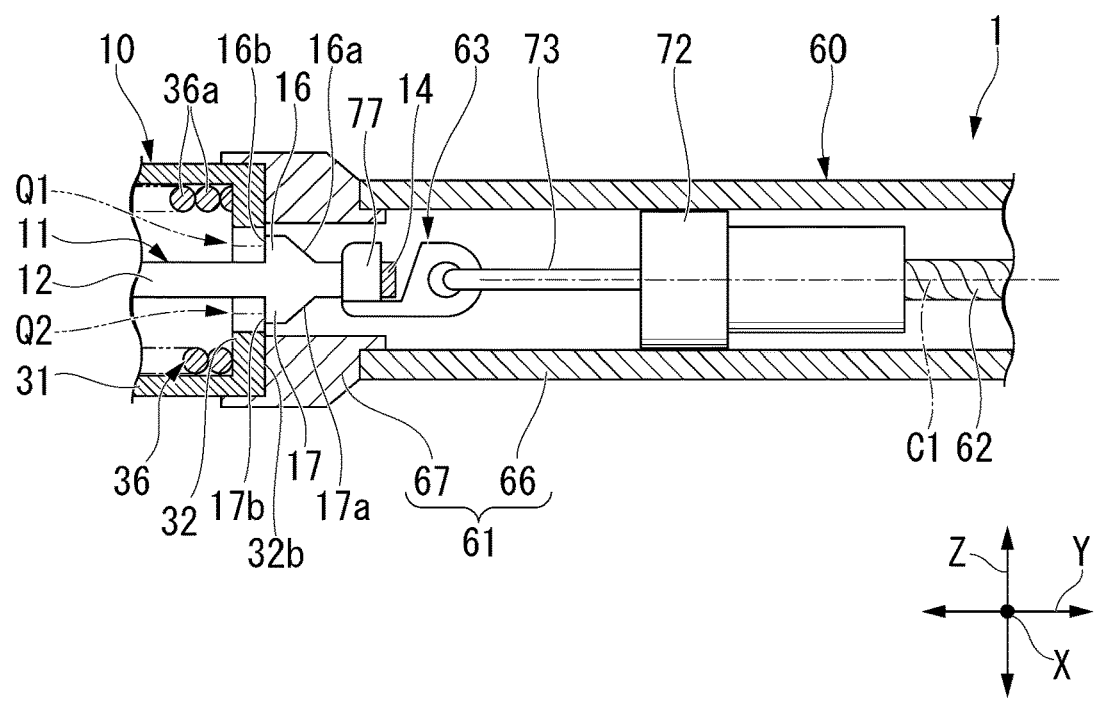
FIG. 13 is a cross-sectional planar view schematically showing the locking state of the endoscope clip according to the present embodiment.
Figure 14:
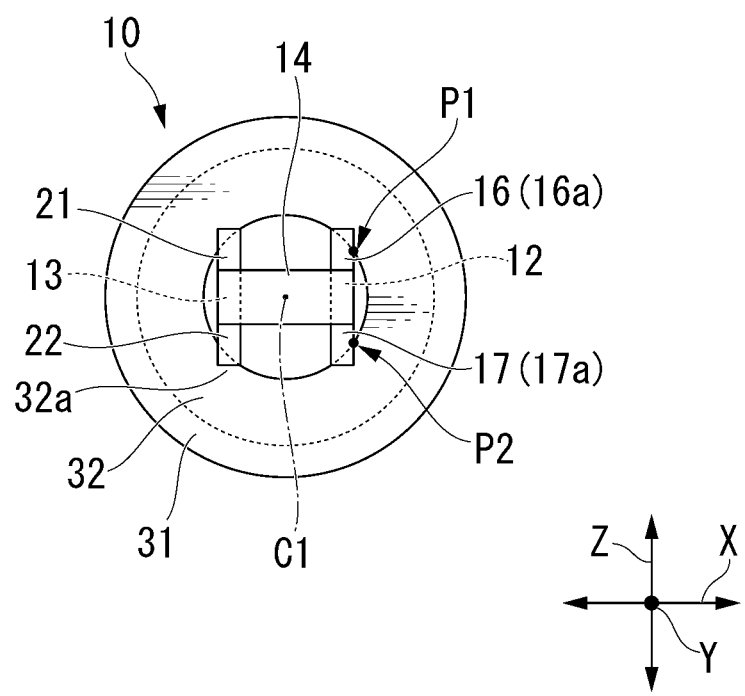
FIG. 14 is a view schematically showing a state of the endoscope clip in FIG. 12 viewed from the proximal end side.

As shown in FIGS. 12 and 13, when the clip 10 is in the locking state, the strand 36a of the elastic member 36 that is compressed in the axial direction Y enters a close winding state in which the strands 36a adjacent to each other in the axial direction Y are in almost close contact with each other. When the clip 10 is in the locking state, the distal end surfaces 16b, 17b of the first engaged portions 16, 17 are locked (for example, engaged) to the proximal end surface 32b of the engaging portion 32 such that the movement of the arm portion 11 toward the distal end side of the arm portion 11 with respect to the pressing tube 31 is restricted. That is, the state in which the clip 10 ligates the target tissue T is maintained, and the first arm 12 and the second arm 13 are impossible to return to the initial state. In other words, when the arm portion 11 is in the locking state, the distal end surfaces 16b, 17b of the first locked portions 16, 17 are locked by the proximal end surface 32b of the locking portion 32 such that the transition of the arm portion 11 from the closed configuration to the first open configuration or the transition from the closed configuration to the second open configuration are restricted. In the clip 10, the arm portion 11 is fixed in the closed configuration. The central portion 14 is positioned at the proximal end side more than the pressing tube 31 and protrudes.

Subsequently, the operator separates the clip 10 ligating the target tissue T from the treatment tool main body 40.

Figure 15:
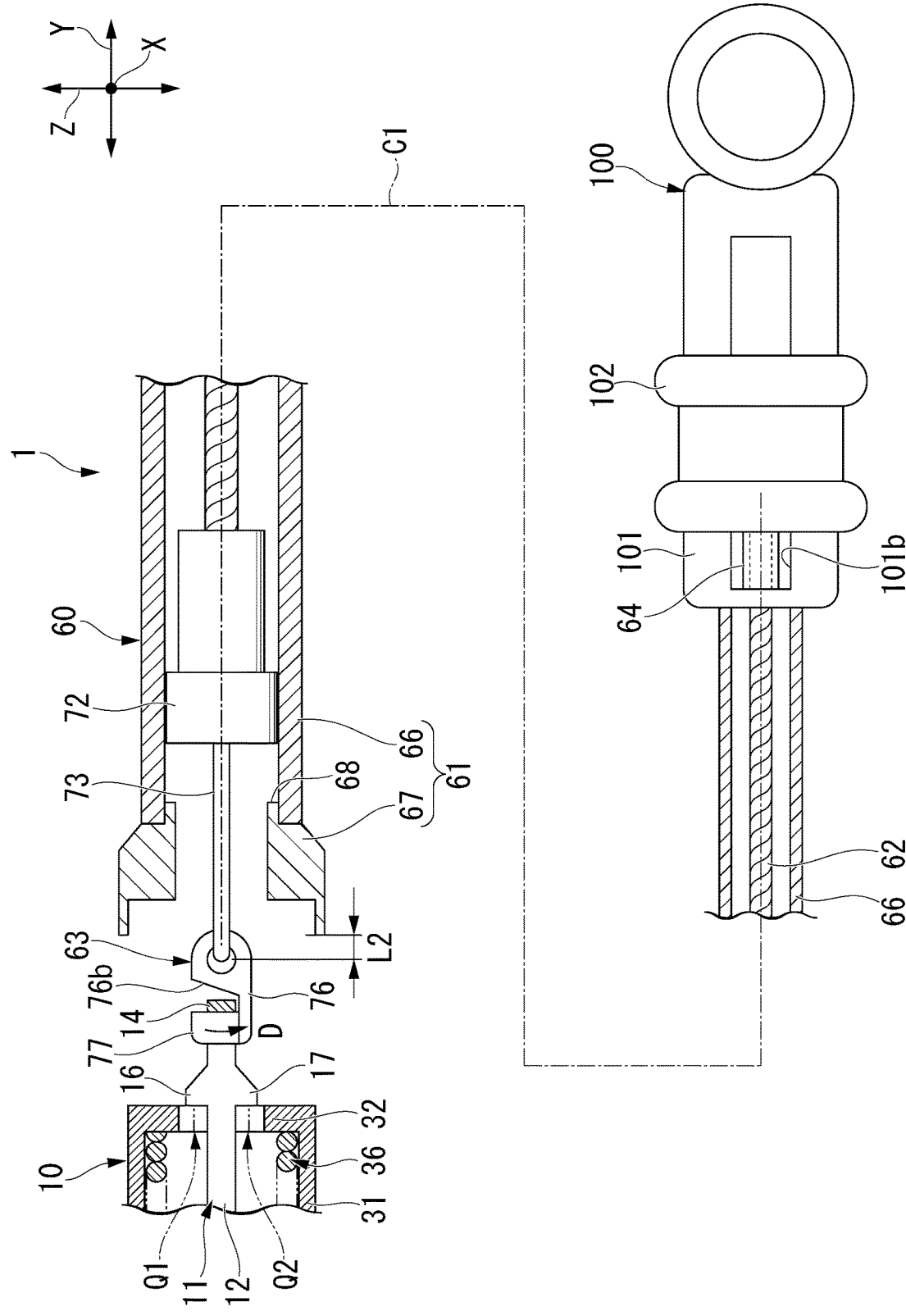
FIG. 15 is a view schematically showing medical procedures for indwelling the endoscope clip according to the present embodiment in the body.

When the operator pushes the slider 102, the operation wire 62 moves to the distal end side with respect to the coil sheath 66. As shown in FIG. 15, when the slider 102 is pushed to be in contact with the limiter 64, the loop portion 73 protrudes at the length L2 as the maximum protrusion amount with respect to the distal member 67.

In the case of removing the limiter 64, when the slider 102 is pushed such that the distal end surface of the enlarged diameter portion 72 comes in contact with the step portion 68, the loop portion 73 protrudes at an amount larger than the length L2 with respect to the distal member 67.

Figure 16:
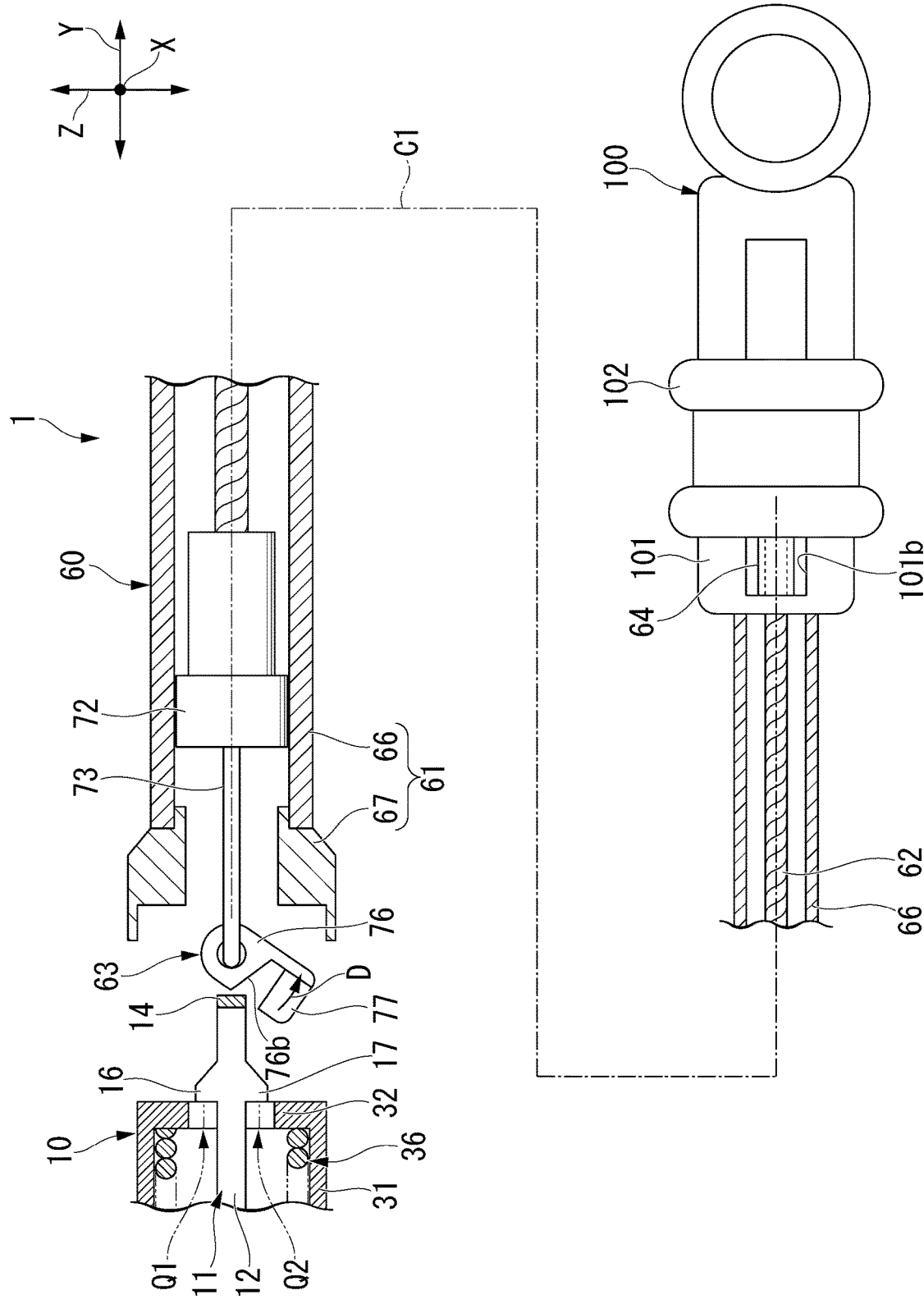
FIG. 16 is a view schematically showing medical procedures for indwelling the endoscope clip according to the present embodiment in the body.

As shown in FIG. 15, when the connection member 63 protrudes toward the distal side more than the distal member 67, the arm portion 11 and the pressing tube 31 move integrally toward the distal end side. Since the connection member 63 is located outside the pressing tube 31, the connection member 63 may rotate with respect to the loop portion 73. When the operator pushes the slider 102 to move the operation wire 62 toward the distal end side, the inclined surface 76b of the connection member 63 comes into contact with the proximal end surface of the central portion 14 of the clip 10 that ligates the target tissue T. As shown in FIG. 16, the hook 77 rotates in the direction D together with the connecting portion main body 76 by being guided by the inclined surface 76b, and the engagement between the hook 77 and the central portion 14 is released. At this time, the clip 10 maintains the closed configuration.

As a result, the clip 10 ligating the target tissue T is indwelled in the body.

After the clip 10 ligating the target tissue T is indwelled in the body, the operator pulls back the slider 102 to accommodate the connection member 63 in the sheath 61. Subsequently, the operator pulls out and removes the endoscope clip 1 from the channel of the endoscope. Finally, the operator takes necessary measures and ends the series of procedures.

(Effect of Endoscope Clip 1)

Hereinafter, the effect of the endoscope clip 1 according to the present embodiment will be described.

The arm portion 11 of the clip 10 according to the present embodiment has the first arm 12 and the second arm 13.

The arm portion 11 has the closed configuration in which the distal end portion of the first arm 12 and the distal end portion of the second arm 13 are in contact with each other, the first open configuration in which the distal end portion of the first arm 12 and the distal end portion of the second arm 13 are separated from each other by the first distance W1, and the second open configuration in which the distal end portion of the first arm 12 and the distal end portion of the second arm 13 are separated from each other by the first distance W2.

When the limiter 64 is arranged in the slit 101b of the operation portion main body 101 while covering the operation wire 62, the movable range of the slider 102 in the slit 101b is restricted by the limiter 64. When the limiter 64 is removed from the slit 101b, the slider 102 may advance and retract in the entire range of the slit 101b. That is, the limiter 64 is configured to restrict the relative movement of the slider 102 with respect to the operation portion main body 101 in the slit 101b of the operation portion main body 101.

When the slider 102 moves with respect to the operation portion main body 101, the operation wire 62 connected to the slider 102, the enlarged diameter portion 72, the loop section 73, the hook 77, and the arm portion 11 connected to the operation wire move with respect to the operation unit main body 101. According to the present embodiment, when the arm portion 11 moves with respect to the operation portion main body 101, the arm portion 11 also moves with respect to the pressing tube 31 of the treatment tool main body 40. As described above, when the arm portion 11 moves relative to the pressing tube 31, the first arm 12 and the second arm 13 of the arm portion 11 come in contact with the distal end portion of the pressing tube 31 and the opening width of the arm portion 11 changes.

Accordingly, according to the present embodiment, the limiter 64 may restrict the relative movement of the arm portion 11 with respect to the operation portion main body 101 and restrict the opening width of the arm portion 11.

When the endoscope clip 1 according to the present embodiment is manufactured, if the relationship between the dimension of the limiter 64 and the opening width of the arm portion 11 is checked in advance, it is possible to prepare several variations of the endoscope clip 1 corresponding to the various sizes of the target tissue T as the treatment target is determined so as to realize the quick response with respect to different treatment targets.

According to the present embodiment, when the limiter 64 is disposed in the slit 101b and the slider 102 is in contact with the limiter 64, the first arm 12 and the second arm 13 are in the half-opened first open configuration. In this state, the operator is impossible to further advance the slider 12. Accordingly, the first arm 12 and the second arm 13 are impossible to be transitioned (moved) from the first open configuration to the second open configuration due to the contact of the slider 102 and the limiter 64.

On the other hand, in the state in which the limiter 64 is removed, when the operator further advances the slider 102 to cause the slider 102 to come in contact with the distal end surface of the slit 101b, the first arm 12 and the second arm 13 become the full-opened second open configuration.

By providing the limiter 64 corresponding to the size of the target tissue T that is most often treated as the treatment target, during the actual treatment, when the orientation and the opening width of the clip 10 are adjusted corresponding to the target tissue T, the operation for the operator to adjust the endoscope clip 1 may be shortened such that the maneuverability, the operation time, and the efficiency may be improved.

The limiter 64 has a simple configuration and is easy to be manufactured such that the endoscope clip 1 applicable to various treatment targets may be configured at low cost.

(First Modification)

Hereinafter, an endoscope clip 1A according to a first modification of the present embodiment will be described. Description of the same configuration with the endoscope clip 1 according to the above-described first embodiment will be omitted, and the different points from the first embodiment will be focused on and described.

Figure 20:
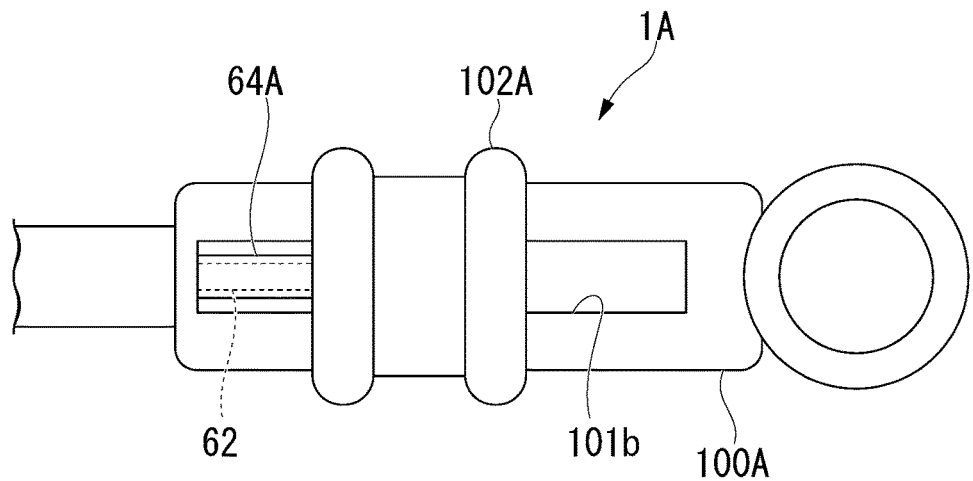
FIG. 20 is a lateral view schematically showing an operation portion of an endoscope clip according to a first modification of the first embodiment of the present disclosure.
Figure 21:
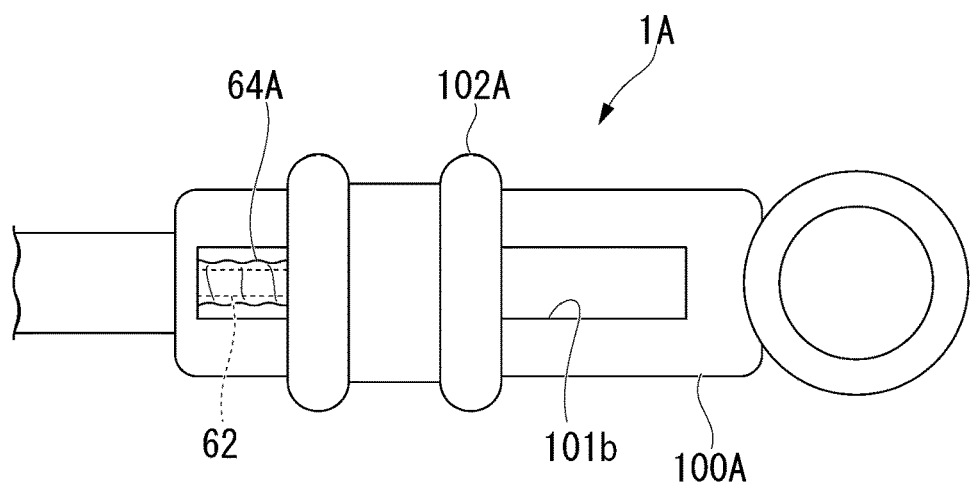
FIG. 21 is a schematic view describing the procedures of using the endoscope clip according to the first modification of the first embodiment of the present disclosure.

FIG. 20 is a perspective view schematically showing an operation portion 100 of the endoscope clip 1A according to the present modification. FIG. 21 is a schematic view showing the procedures using the endoscope clip 1A.

The endoscope clip 1A according to the present modification is different in the configuration of the operation portion 100A when compared with the endoscope clip 1 of the above-described first embodiment. As shown in FIG. 20, the operation portion 100A of the endoscope clip 1A according to the present modification has a limiter 64A instead of the limiter 64 according to the first embodiment.

The limiter 64 of the endoscope clip 1 according to the first embodiment of the present disclosure is formed of the resin material having the rigidity that the limiter 64 is not compressed even the certain pressure is applied in the longitudinal axis direction of itself. Compared to this configuration, the limiter 64A of the endoscope clip 1A according to the present modification is formed of a material capable of being elastically deformed by a certain degree when the pressure in the longitudinal axis direction is applied thereto. In a state in which the pressure in the longitudinal axis direction is not applied, the limiter 64A is formed in the same dimension as that of the limiter 64 according to the first embodiment. As shown in FIG. 20, in the state in which the slider 102 is in contact with the limiter 64A, the arm portion 11 of the endoscope clip 1A is in the half-opened first open configuration. In other words, as this time, the opening width of the arm portion 11 of the clip 1A is the first distance W1.

Different from the endoscope clip 1 according to the first embodiment, according to the endoscope clip 1A of the present modification, the operator may further advance the slider 102A. Due to the force by the operator pushing the slider 102A, the limiter 64A in contact with the slider 102A is compressed in the longitudinal axis direction and elastically deformed. As shown in FIG. 21, the dimension of the elastically deformed limiter 64 in the longitudinal axis direction decreased such that the movable range of the slider 102A in the slit 101*b* increases by an amount equal to the decreased dimension of the limiter 64A. As a result, the arm portion 11 of the endoscope clip 1A may be further opened from the half-opened first open configuration. The arm portion of the endoscope clip 1A according to the present modification may be transitioned to a configuration having a slightly larger opening width that that of the first open configuration. However, the opening width of the arm portion 11 at this time is smaller than the second distance W2 as the opening width of the second open configuration.

Accordingly, the endoscope clip 1A according to the present modification is applicable to the target tissue T having an intermediate size between the first distance W1 and the second distance W2.

In a state in which even the operator pushes the slider 102 that the limiter 64A reaches the limitation of the elastic deformation and the opening width of the arm portion 11 is still smaller than the size of the target tissue T, the operator may detach the limiter 64A to resolve the problem.

Other configurations of the endoscope clip 1A according to the present modification are the same with that of the endoscope clip 1 according to the first embodiment. By the same operations as the procedures described in the first embodiment, it is possible to indwell the target tissue T using the endoscope clip 1A. According to the endoscope clip 1A according to the present embodiment, it is possible to efficiently treat the target tissue T with an intermediate size between the first distance W1 and the second distance W2.

(Second Modification)

Hereinafter, an endoscope clip 1B according to a second modification of the present embodiment will be described. Description of the same configuration with the endoscope clip 1 according to the above-described first embodiment will be omitted, and the different points from the first embodiment will be focused on and described.

Figure 22:
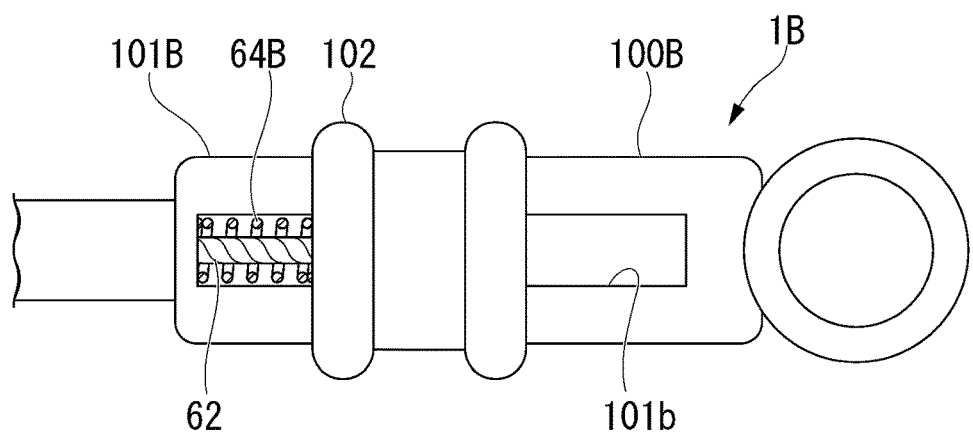
FIG. 22 is a lateral view schematically showing an operation portion of an endoscope clip according to a second modification of the first embodiment of the present disclosure.

FIG. 22 is a lateral view schematically showing an operation portion 100B of an endoscope clip 1B according to the present modification. As shown in FIG. 22, a spring 64B connecting the distal end surface of the slit 101*b* of the operation portion main body 101B and the distal end surface of the slider 102 is disposed in the operation portion 100B according to the present modification. A method of connecting the spring 64B to the distal end surface of the slit 101*b* of the operation portion main body 101B and the distal end surface of the slider 102 is not particularly limited and various conventional methods may be used.

The spring 64B according to the present modification has a free length same as the length of the limiter 64 according to the first embodiment in the state where no external force applies. Accordingly, in the present modification, the slider 102 is at the same position as the position where the slider 102 contacts the limiter 64 according to the first embodiment when the operator does not operate the slider 102. That is, according to the endoscope clip 1B according to the present modification, in the state in which the operator does not operate the slider 102, the first open configuration of the arm portion 11 is maintained and the first arm 12 and the second arm 13 are separated from each other by the first distance W1.

As described above, it is disclosed that the spring 64B in the state in which the external force is not applied has the same free length with the length of the limiter 64 according to the first embodiment. Actually, in the state in which the arm portion 11 is in the first open configuration, the slider 102 receives a force toward the distal end side due to a resistance force F1 due to the coil spring 36 and a self-expanding force of the arm portion 11 such that the spring 64 is compressed. However, in the present modification, the compress amount of the spring 64B at this time is minute such that the spring 64B in the state in which the external force is not applied is considered to have the same free length with the length of the limiter 64 according to the first embodiment.

In the state in which the arm portion 11 is in the first open configuration, the resistance force F1 by the coil spring 36 and the resistance force F2 due to the self-expanding force of the arm portion 11 are applied to the slider 102. In order to maintain the state in which the arm portion 11 is in the first configuration, it is necessary to apply a force for pushing back the slider 102 that is equal to a sum of the resistance force F1 and the resistance force F2. Accordingly, a resistance force F3 by the spring 64B when the arm portion 11 is in the first open configuration has to be equal to the sum of the resistance force F1 and the resistance force F2. However, actually, the resistance force F3 of the spring 64B to push back the slider is reduced due to the friction between the operation wire 62 and the coil sheath 66. Accordingly, the resistance force F3 has to be larger than the sum of the resistance force F1 and the resistance force F2.

In other words, the resistance force F3 by the spring 64B in the state in which the arm portion 11 is in the first open configuration is larger than the resistance force F1 by the coil spring 36 in the state in which the arm portion 11 is in the first open configuration. Also, the resistance force F3 by the spring 64B in the state in which the arm portion 11 is in the first open configuration is larger than the resistance force F2 due to the self-expanding force of the arm portion 11 in the state in which the arm portion 11 is in the first open configuration.

Other configurations of the endoscope clip 1B according to the present modification are the same with that of the endoscope clip 1 according to the first embodiment. By the same operations as the procedures described in the first embodiment, it is possible to indwell the target tissue T using the endoscope clip 1B.

Second Embodiment

Hereinafter, an endoscope clip 2 according to a second embodiment of the present disclosure will be described with reference to FIG. 23A, FIG. 23B, and FIG. 24. In the following description, the same configuration elements will be designated with the same reference signs and the description will be omitted.

Figure 23A:
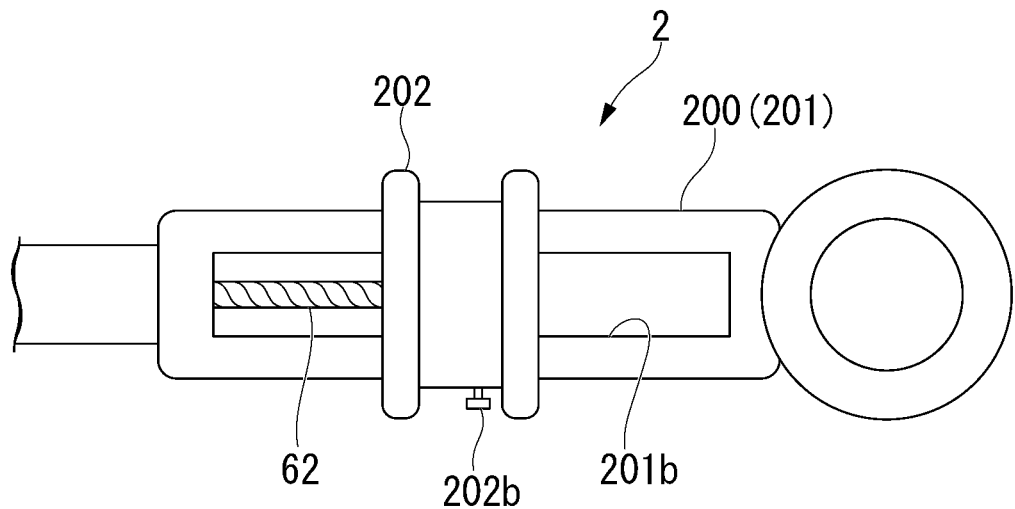
FIG. 23A is a lateral view schematically showing an operation portion of an endoscope clip according to a second embodiment of the present disclosure.

FIG. 23A is a lateral view schematically showing an operation portion 200 of the endoscope clip 2 according to the present embodiment. FIG. 23B is a partial enlarged cross-sectional view showing the operation portion 200 of the endoscope clip 2 according to the present embodiment. FIG. 24 is a schematic view showing the procedures using the endoscope clip 2 according to the present embodiment.

The endoscope clip 1 according to the first embodiment has the configuration to restrict the advancement of the slider 102 by the slider 102 and the limiter 64 contacting with each other. On the other hand, as shown in FIGS. 23A and 23B, the endoscope clip 2 according to the second embodiment of the present disclosure has a configuration to limit the advancement of the slider 202 with respect to the operation unit main body 201 by using a ratchet mechanism.

Figure 23B:
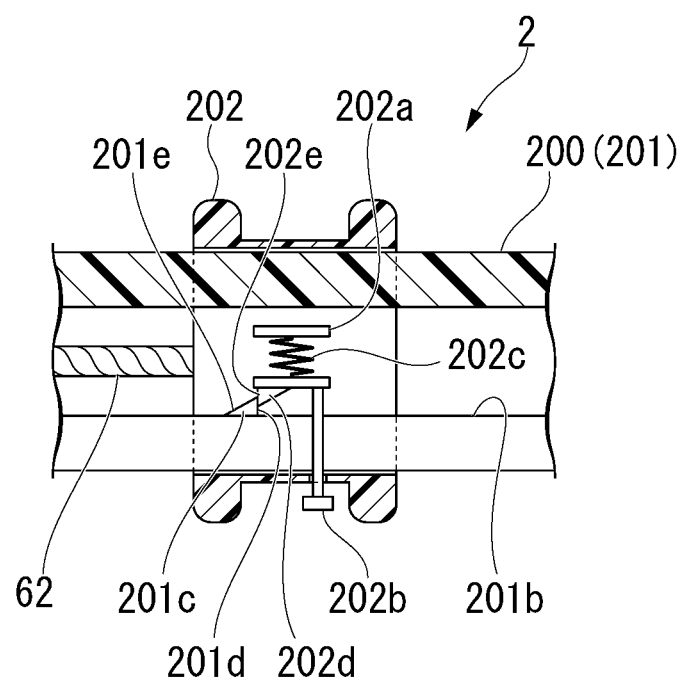
FIG. 23B is an enlarged cross-sectional view showing part of the operation portion of the endoscope clip according to the present embodiment.
Figure 24:
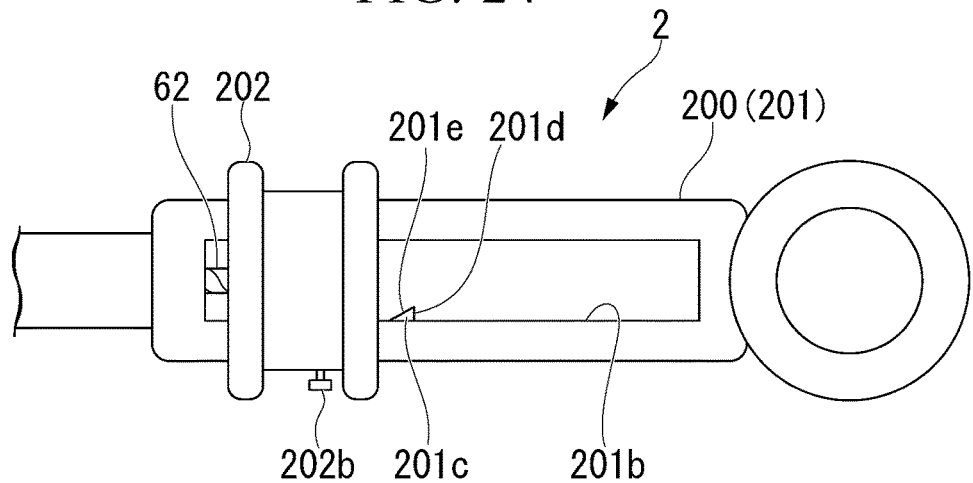
FIG. 24 is a schematic view describing the procedures of using the endoscope clip according to the present embodiment.

More specifically, as shown in FIG. 23A and FIG. 23B, in the endoscope clip 2 according to the present embodiment, a protrusion (first protrusion) 201c is disposed on an inner circumferential surface of the slit 201b of the operating portion main body 201, and a ratchet mechanism 202a is provided in the slider 202. The ratchet mechanism 202a of the slider 202 has a button 202b, a spring 202c, and a protrusion (second protrusion) 202d.

As shown in FIG. 23B, according to the present embodiment, the protrusion 201c has a right triangle shape in a cross section taken along a plane passing through the central axis of the slit 201b. The protrusion 201c has a wall portion 201d formed to be orthogonal to the inner circumferential surface of the slit 201b, and an inclined portion 201e formed in an inclined surface shape. The inclined portion 201e is sequentially separated from the inner circumferential surface of the slit 201b toward the proximal end of the operation portion main body 201. A connection portion between the wall portion 201d and the inclined portion 201e is located at a position having the largest distance from the inner circumferential surface of the slit 201b in the protrusion 201c. The distance from the inner circumferential surface of the slit 201b to the connecting portion between the wall portion 201d and the inclined portion 201e is defined as a height of the protrusion 201c. The distance from the wall 201d to the distal end surface of the slit 201b is equal to the length of the limiter 64 of the endoscope clip 1 in the longitudinal axis direction according to the first embodiment.

The protrusion 202d of the ratchet mechanism 202a has a wall portion 202e formed in parallel with the wall portion 201d of the protrusion 201c and an inclined portion 202f formed in an inclined surface shape. The spring 202c of the ratchet mechanism 202a biases the protrusion 202d in the radial direction such that when the operator advances the slider 202 along the central axis direction of the endoscope clip 2, the wall portion 201d and the wall portion 202e are in contact with each other. In this state, even if the operator further pushes the slider 202 toward the distal end side, the slider 202 does not move forward due to the contact and engagement between the wall portion 201d and the wall portion 202e. That is, the advancement of the slider 202 along the central axis of the operation portion main body 201 is restricted by the protrusion 201c and the protrusion 202d engaging with each other.

In this state, the position of the slider 202 is the same as the position of the slider 102 when the arm portion 11 of the endoscope clip 1 according to the first embodiment described above is in the first open configuration. That is, according to the present embodiment, the protrusion 201c of the slit 201b and the protrusion 202d of the slider 202 are engaged with each other such that arm portion 11 is in the first open configuration in which the opening width between the first arm 12 and the second arm 13 is the first distance W1, and the transition from the first open configuration to the second open configuration is restricted.

When the operator confirms that the distance between the first arm 12 and the second arm 13 is smaller than the dimension of the target tissue T, it is necessary for the operator to enlarge the opening width of the arm portion 11. At this time, the operator has to further advance the slider 202 from the position of the protrusion 201c of the operation portion main body 201.

In the state in which the protrusion 201c of the slit 201b and the protrusion 202d of the slider 202 are engaged with each other, when the operator pushes the button 202b of the ratchet mechanism 202a, the protrusion 202d of the ratchet mechanism 202a moves in the radial direction of the operation portion main body 201 (the direction intersecting the longitudinal axis direction of the part). As a result, the engagement state between the protrusion 201c of the slit 201b and the protrusion 202d of the slider 202 is released, and the slider 202 may be advanced along the central axis of the operation portion main body 201. As shown in FIG. 24, the operator may further advance the slider 202 to enlarge the opening width of the first arm 12 and the second arm 13 to the second distance W2. By such an operation, the operator may cause the arm portion 11 to be transitioned from the first open configuration to the second open configuration.

In the state in which the slider 202 exceeds the protrusion 201c of the slit 201b, the operator pulls the slider 202 toward the proximal end side such that the inclined portion 202*f* of the protrusion 202*d* may move to the proximal end side while contacting the inclined surface of the protrusion 201*c*. As a result, the arm portion 11 may be transitioned from the second open configuration to the first open configuration again only by the operation of the operator pulling the slider 202 toward the proximal end side.

According to the present embodiment, an example in which the protrusion 201*c* of the slit 201*b* and the protrusion 202*d* of the slider 202 have the right triangle shape in cross section has been described; however, the configuration of the endoscope clip 2 is not limited thereto. The endoscope clip 2 according to the present embodiment only has to have a configuration in which the slider 202 cannot relatively advance with respect to the operation section body 201 due to the engagement between the operation portion main body 201 and the slider 202. The specific aspect of the engagement between the operation portion main body 201 and the slider 202 is not particularly limited.

Other configurations of the endoscope clip 2 according to the present embodiment are the same with that of the endoscope clip 1 according to the first embodiment. By the same operations as the procedures described in the first embodiment, it is possible to indwell the target tissue T using the endoscope clip 2.

Third Embodiment

Hereinafter, an endoscope clip 3 according to a third embodiment of the present disclosure will be described with reference to FIG. 25A, FIG. 25B, and FIG. 26.

Figure 25A:
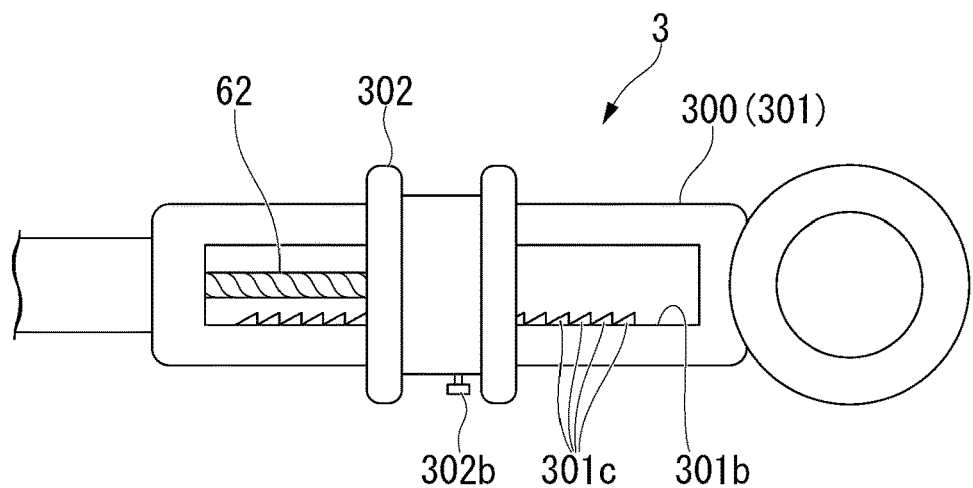
FIG. 25A is a lateral view schematically showing an operation portion of an endoscope clip according to a third embodiment of the present disclosure.
Figure 25B:
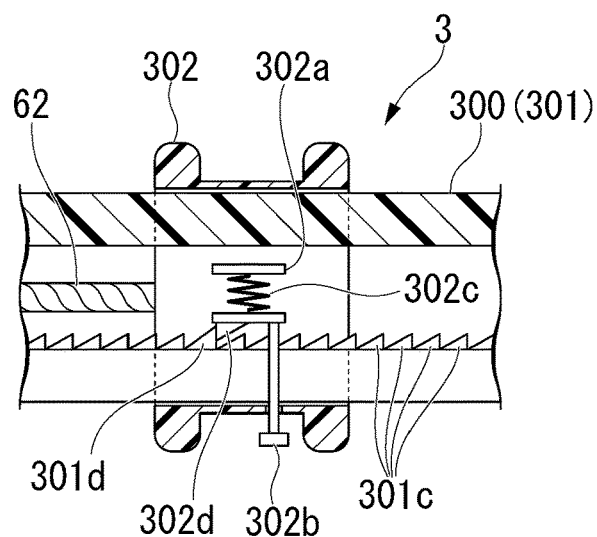
FIG. 25B is an enlarged cross-sectional view showing part of the operation portion of the endoscope clip according to the present embodiment.
Figure 26:
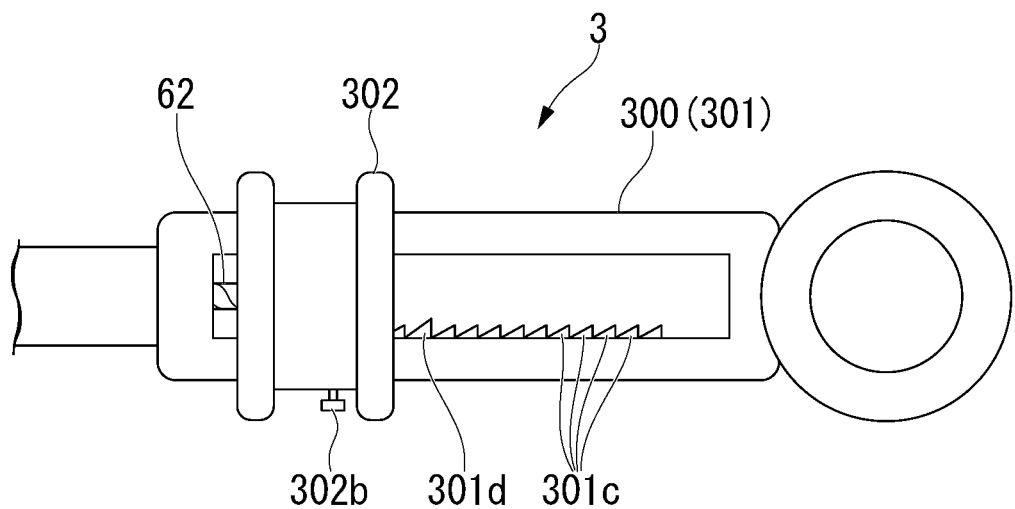
FIG. 26 is a schematic view describing the procedures by using the endoscope clip according to the present embodiment.

FIG. 25A is a lateral view schematically showing an operation portion 300 of the endoscope clip 3 according to the present embodiment. FIG. 25B is a partial enlarged cross-sectional view of the operation portion 300 of the endoscope clip 3 according to the present embodiment. FIG. 26 is a schematic view showing the procedures using the endoscope clip 3 according to the present embodiment.

As shown in FIG. 25A, in the endoscope clip 3 according to the present embodiment, a plurality of small protrusions (first protrusions) 301*c* and a large protrusion (third protrusion) 301*d* are formed on the inner circumferential surface of the slit 301*b* of the operation portion main body 301 along the longitudinal axis direction of the operation portion main body 301. Each of the plurality of small protrusions 301*c* has the same configuration as the protrusion 201*c* of the endoscope clip 2 according to the second embodiment. The large protrusion 301*d* has a cross-section in a right-angled triangular shape that is taken along a plane passing through the central axis of the slit 301*b*, and has a height higher than that of the small protrusions 301*c*. For example, the large protrusion 301*d* may have the height twice of that of the small protrusion 301*c*. According to the present modification, the distance from the wall portion of the large protrusion 301*d* to the distal end surface of the slit 301*b* is equal to the length of the limiter 64 of the endoscope clip 1 in the longitudinal axis direction according to the first embodiment.

The slider 302 according to the present modification has a ratchet mechanism 302*a*. The ratchet mechanism 302*a* has a button 302*b*, a spring 302*c*, and a protrusion (second protrusion) 302*d*. According to the present embodiment, the button 302*b* of the ratchet mechanism 302*a* may be pushed in two stages. For example, when the operator half-presses the button 302*b* of the ratchet mechanism 302*a* according to the present embodiment with a force equivalent to the force of pushing the button 202*b* of the ratchet mechanism 202*a* according to the second modification, the engagement between the protrusion 302*d* of the ratchet mechanism 302*a* and the small protrusions 301*c* of the operation portion main body 301 may be released. The operator may release the engagement between the protrusion 302*d* of the ratchet mechanism 302*a* and the large protrusion 301*d* of the operation portion main body 301 by fully pressing the button 302*b* of the ratchet mechanism 302*a*.

According to the endoscope clip 3 100D according to the present embodiment, when the operator once half-presses the button 302*b* of the ratchet mechanism 302*a*, the slider 302 may be advanced along the longitudinal axis direction of the operation portion main body 301 until the protrusion 302*d* of the ratchet mechanism 302*a* contacts the next small protrusion 301*c*. Accordingly, when the plurality of small protrusions 301*c* are continuously disposed on the inner circumferential surface of the operation portion main body 301, the slider 302 may advance at only a certain distance for each time when the operator half-presses the button 302*b*.

On the other hand, the operator may advance the slider 302 along the longitudinal axis direction of the operation section body 301 by continuing half-pressing the button 302*b* of the ratchet mechanism 302*a*. In this case, the operator may advance the slider 302 until the protrusion 302*d* of the ratchet mechanism 302*a* contacts the large protrusion 301*d*. When the protrusion 302*d* of the ratchet mechanism 302*a* comes into contact with the large protrusion 301*d*, as described above, the opening width between the first arm 12 and the second arm 13 becomes the first distance W1, and the arm portion 11 of the endoscope clip 3 is in the half-opened first open configuration.

When the arm portion 11 of the endoscope clip 3 is in the first open configuration, even if the operator pushes the slider 302 along the longitudinal axis direction of the operation section main body 301 in a state in which the arm portion 11 is in the first open configuration, due to the engagement of the protrusion 302*d* of the ratchet mechanism 302*a* and the large protrusion 301*d* of the operation section main body 301, the movement of the slider 302 toward the distal end side is restricted, and the transition of the arm portion 11 from the first open configuration to the fully open second open configuration is restricted.

In this case, by the operator fully pushing the button 302*b* of the ratchet mechanism 302*a*, the protrusion 302*d* of the ratchet mechanism 302*a* moves in the radial direction of the operation section main body 301 and climbs on and overcomes the large protrusion 301*d* of the operation section main body 301. Accordingly, as shown in FIG. 26, the engagement of the protrusion 302*d* of the ratchet mechanism 302*a* and the large protrusion 301*d* of the operation portion main body 301 is released, and the operator may further advance the slider 302. As a result, in the endoscope clip 3 according to the present embodiment, the opening width between the first arm 12 and the second arm 13 of the arm portion 11 may be further enlarged from the first distance W1 to the second distance W2. That is, the operator may cause the arm portion 11 of the endoscope clip 3 according to the present embodiment to be transitioned from the first open configuration to the second open configuration.

Other configurations of the endoscope clip 3 according to the present embodiment are the same with that of the endoscope clip 1 according to the first embodiment. By the same operations as the procedures described in the first embodiment, it is possible to indwell the target tissue T using the endoscope clip 3.

According to the endoscope clip 3 according to the present embodiment, the slider 302 can move forward substantially the same distance each time the operator half-presses the button 302b of the ratchet mechanism 302a of the slider 302. Accordingly, the operator may finely adjust the opening width of the arm portion 11 by a simple operation.

(Modification)

Figure 27:
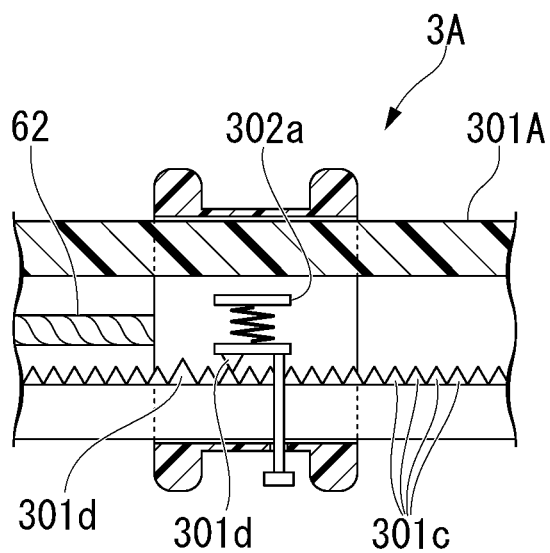
FIG. 27 is a cross-sectional side view schematically showing part of an operation portion of an endoscope clip according to a modification of the third embodiment of the present disclosure.

Hereinafter, an endoscope clip 3A according to a modification of the third embodiment of the present disclosure will be described with reference to FIG. 27.

In the endoscope clip 3A according to the present modification, a plurality of small protrusions (first protrusions) 301c and a single large protrusion (third protrusion) 301d formed on the inner circumferential surface of the slit 301b of the operation unit body 101C along the longitudinal axis direction of the operation portion main body 101C. The plurality of small protrusions 301c and the large protrusion 301d have a cross section in a substantially equilateral triangular shape. The slider 302A of the endoscope clip 3A according to the present embodiment includes a ratchet mechanism 302a having a protrusion (second protrusion) 302d formed in a substantially equilateral triangle shape.

The endoscope clip 3A according to the present modification has the above-described configuration such that when the operator pushes the slider 302 toward the distal end side along the central axis direction of the operation portion main body 101C, the protrusion 302d of the slider 302 moves toward the distal end side along the inclined portion of the small protrusion 301c contacting the protrusion 302d of the slider 302 and climbs on and overcomes the small protrusion 301c.

In the endoscope clip 3A according to the present modification, the large protrusion 301d has a height such that it is impossible for the protrusion 302d to overcome the protrusion 301d due to the pressing force by the operator along the central axis direction of the operation portion main body 101C. Accordingly, when the slider 302A advances to a position to come in contact with the large protrusion 301d, it is necessary for the operator to fully push the button 302b of the ratchet mechanism 302a. When the operator fully pushes the button 302b of the ratchet mechanism 302a and advances the slider 302A toward the distal end side, the restriction due to the engagement of the protrusion 302d of the ratchet mechanism 302a and the large protrusion 301d may be released.

In the above description, the plurality of small protrusions 301c and the large protrusion 301d provided on the operation portion main body 301A and the protrusion 302d of the ratchet mechanism 302a have been described to have a substantially equilateral triangular cross-sectional shape; however, the configuration is not limited thereto. For example, in the endoscope clip 3A according to the present modification, each of the plurality of small protrusions 301c, the one large protrusion 301d, and the protrusion 302d may have a cross section formed in an isosceles triangle shape.

Other configurations of the endoscope clip 3A according to the present modification are the same with that of the endoscope clip 1 according to the first embodiment. By the same operations as the procedures described in the first embodiment, it is possible to indwell the target tissue T using the endoscope clip 3A.

According to the endoscope clip 3A according to the present modification, there is no necessity to differentiate the half-pressing operation and the full-pressing operation at the button 302b of the ratchet mechanism 302a, and it is possible to prevent any operation mistake.

Although the respective embodiments and modifications of the present invention have been described above, the technical scope of the present invention is not limited to the above-described embodiments, and configurations in the respective embodiments and modifications within the scope not departing from the spirit of the present invention. It is possible to change the combination of elements, make various changes to each constituent element, or delete each constituent element. For example, the configuration according to any one of above-described embodiments and modifications of the present disclosure may be appropriately combined with each modification of the operation section. The present disclosure is not limited by the above description, but only by the appended claims.

According to the first embodiment of the present invention, the example in which the limiter 64 is disposed on the distal side of the slider 102 has been described. However, the position where the limiter 64 is disposed is not particularly limited as long as the advanceable range of the slider 102 along the longitudinal axis direction of the operation portion 100 may be restricted by the engagement between the limiter 64 and the slider 102.

According to the first embodiment of the present invention, the example in which the limiter 64 is made of a resin material has been described. However, the limiter 64 only has to be formed with a rigidity that the limiter 64 is not compressed even if a constant pressure in the longitudinal axis direction is applied to the limiter 64 itself. The material forming the limiter 64 is not particularly limited. For example, the limiter 64 may be a metallic tubular member.

What is claimed is:

1. An endoscope clip, comprising:
    a clip arm having a first arm and a second arm, the clip arm configured to be transitioned between
        a closed configuration in which the first arm and the second arm are closed,
        a first open configuration in which the first arm and the second arm are separated from each other by a first distance larger than a distance between the first arm and the second arm in the closed configuration, and
        a second open configuration in which the first arm and the second arm are separated from each other by a second distance larger than the first distance;
    a handle;
    a slider configured to operate the clip arm to be transitioned between the closed configuration, the first open configuration, and the second open configuration by moving relative to the handle;
    a limiter configured to restrict the relative movement of the slider with respect to the handle so as to restrict transition of the clip arm from the first open configuration to the second open configuration; and
    a pressing tube having a lumen configured to receive the clip arm,
    wherein when the clip arm enters the pressing tube, the clip arm is deformed as a consequence of the clip arm engaging with an inner wall of the lumen such that the first arm and the second arm approach each other, and
    wherein the clip arm is deformed by engaging with the inner wall of the lumen in the first open configuration, and the deformation due to the pressing tube is removed in the second open configuration.

2. The endoscope clip according to claim 1, further comprising a wire configured to connect the clip arm with the slider and operate the clip arm, wherein the limiter is provided in the handle.

3. The endoscope clip according to claim 2, wherein the limiter is detachably attached to the handle and is detachable from the handle.

4. The endoscope clip according to claim 3,
wherein the limiter restricts a movable range of the slider with respect to the handle, and
wherein the restriction to the movable range of the slider with respect to the handle is released when the limiter is detached from the handle.

5. The endoscope clip according to claim 2,
wherein the slider is configured to be movable along a longitudinal axis direction of the handle,
wherein the limiter comprises:
 a first contact surface provided in the handle;
 a second contact surface provided in the slider and contactable with the first contact surface; and
 a movement mechanism configured to move at least either of the first contact surface or the second contact surface in a direction intersecting the longitudinal axis direction of the handle, and
wherein the movable range of the slider with respect to the handle is restricted by the first contact surface and the second contact surface being in contact with each other.

6. The endoscope clip according to claim 1, wherein the limiter is disposed at a more distal position within the endoscope clip than the slider is.

7. The endoscope clip according to claim 6, wherein the slider is configured to operate the clip arm to be transitioned from the closed configuration to the first open configuration due to the relative movement between the slider and the handle in a state in which the movable range of the slider is restricted by the limiter.

8. The endoscope clip according to claim 6, wherein the slider is configured to operate the clip arm to be transitioned into the second open configuration due to the relative movement between the slider and the handle in a state in which restriction to the movable range of the slider by the limiter is released.

9. The endoscope clip according to claim 1,
wherein the clip arm is biased toward a protruding direction from the pressing tube and the clip arm moves toward the protruding direction from the pressing tube when the restriction to the movable range of the slider is released.

10. The endoscope clip according to claim 1, wherein the limiter is formed of a material having elastic restoring force.

11. The endoscope clip according to claim 1, wherein the closed configuration is a configuration in which the first arm is in contact with the second arm.

12. The endoscope clip according to claim 1, wherein the limiter configured to restrict the relative movement of the slider with respect to the handle so as to restrict transition of the clip arm from the first open configuration to the second open configuration, but to allow transition of the clip arm from the closed configuration to the first open configuration.

13. The endoscope clip according to claim 1, wherein the second distance is approximately twice the first distance.

14. An endoscope clip, comprising:
a clip arm;
a sheath through which the clip arm is insertable;
an operation portion configured to operate the clip arm to
 an accommodation configuration in which the clip arm is accommodated in the sheath,
 a first protrusion configuration in which the clip arm protrudes from the sheath at a first clip length from the sheath, and
 a second protrusion configuration in which the clip arm protrudes from the sheath at a second clip length from the sheath that is larger than the first clip length; and
a restrictor configured to selectively restrict the clip arm from being transitioned from the first protrusion configuration to the second protrusion configuration; and
a pressing tube having a lumen configured to receive the clip arm,
wherein when the clip arm enters the pressing tube, the clip arm is deformed as a consequence of the clip arm engaging with an inner wall of the lumen such that the first arm and the second arm approach each other, and
wherein the clip arm is deformed by engaging with the inner wall of the lumen in the first open configuration, and the deformation due to the pressing tube is removed in the second open configuration.

15. The endoscope clip according to claim 14, further comprising a handle, wherein the restrictor comprises:
 a slider configured to cause the clip arm to be transitioned to the accommodation configuration, the first protrusion configuration, and the second protrusion configuration by the slider moving relative to the handle; and
 a limiter configured to restrict the movement of the slider to thereby restrict the clip arm from being transitioned from the first protrusion configuration to the second protrusion configuration.

16. An operation method for a clip, the clip including a clip arm with a first arm and a second arm, the clip arm configured to be transitioned between a closed configuration in which the first arm and the second arm are closed, a first open configuration in which the first arm and the second arm are separated from each other by a first distance larger than a distance between the first arm and the second arm in the closed configuration, and a second open configuration in which the first arm and the second arm are separated from each other by a second distance larger than the first distance, a pressing tube having a lumen configured to receive the clip arm, and a limiter configured to restrict transition of the clip arm from the first open configuration to the second open configuration, the operation method comprising:
 releasing restriction of the limiter;
 when the restriction by the limiter is released, causing the clip arm to move from the first open configuration to the second open configuration;
 deforming the clip arm by inserting the clip arm into the pressing tube to move the clip arm from the second open configuration to the first open configuration; and
 removing the deformation of the clip arm to move the clip arm from the first open configuration to the second open configuration.

17. The operation method for a clip according to claim 16, wherein the clip further comprises an operation portion having the limiter, and wherein the restriction is released by removing the limiter from the operation portion.

18. The operation method for a clip according to claim 16, further comprising:
 grasping tissues in the body by the clip arm when the clip arm is transitioned to the second open configuration; and
 indwelling the clip arm in the body.

* * * * *